United States Patent
Yoshinari et al.

(10) Patent No.: US 7,332,713 B2
(45) Date of Patent: Feb. 19, 2008

(54) MASS SPECTROMETRIC METHOD AND MASS SPECTROMETRIC SYSTEM

(75) Inventors: Kiyomi Yoshinari, Hitachi (JP); Toshiyuki Yokosuka, Hitachi (JP); Atsushi Ootake, Hitachiota (JP); Kinya Kobayashi, Hitachi (JP); Yuichiro Hashimoto, Tachikawa (JP)

(73) Assignee: Hitachi, Ltd., Tokyo (JP)

( * ) Notice: Subject to any disclaimer, the term of this patent is extended or adjusted under 35 U.S.C. 154(b) by 337 days.

(21) Appl. No.: 11/210,965

(22) Filed: Aug. 25, 2005

(65) Prior Publication Data

US 2006/0043281 A1    Mar. 2, 2006

(30) Foreign Application Priority Data

Aug. 27, 2004  (JP)  ............................ 2004-248169

(51) Int. Cl.
*B01D 59/44*    (2006.01)
(52) U.S. Cl. .................. 250/282; 250/288; 250/287; 73/1.01

(58) Field of Classification Search ................ 250/288, 250/282, 287; 73/1.01
See application file for complete search history.

(56) References Cited

FOREIGN PATENT DOCUMENTS

JP    2002-168842    6/2002

*Primary Examiner*—Jack I. Berman
*Assistant Examiner*—Michael J Logie
(74) *Attorney, Agent, or Firm*—Dickstein Shapiro LLP

(57) ABSTRACT

In a method for mass spectrometry, a plurality of juxtaposed chromatography apparatus connected to a mass spectrometer start eluting at a predetermined time difference and the following mass spectrometer conducts mass spectrometry. A chromatogram in a preceding chromatography apparatus is analyzed on real time base and results of the analysis are used on real time base to change an elusion condition of a succeeding chromatography apparatus. A mass spectrometric system suitable for carrying out the method is also provided.

20 Claims, 19 Drawing Sheets

FIG.8

IS TANDEM MASS SPECTROMETRY OPTIMIZATION
BY TIME-DIFFERENCE PARALLEL
LC MONITORING SYSTEM TO BE EXECUTED ?

Yes ●

SPECIFICATIONS OF TIME-DIFFERENCE PARALLEL
LC TANDEM MASS SPECTROMETRIC SYSTEM

- DESIGNATE ELUSION START TIME DIFFERENCE OF PARALLEL LC.

15 MINUTES

- DESIGNATE PEAK DECISION PERIOD IN CHROMATOGRAM.

30 MINUTES

⋮

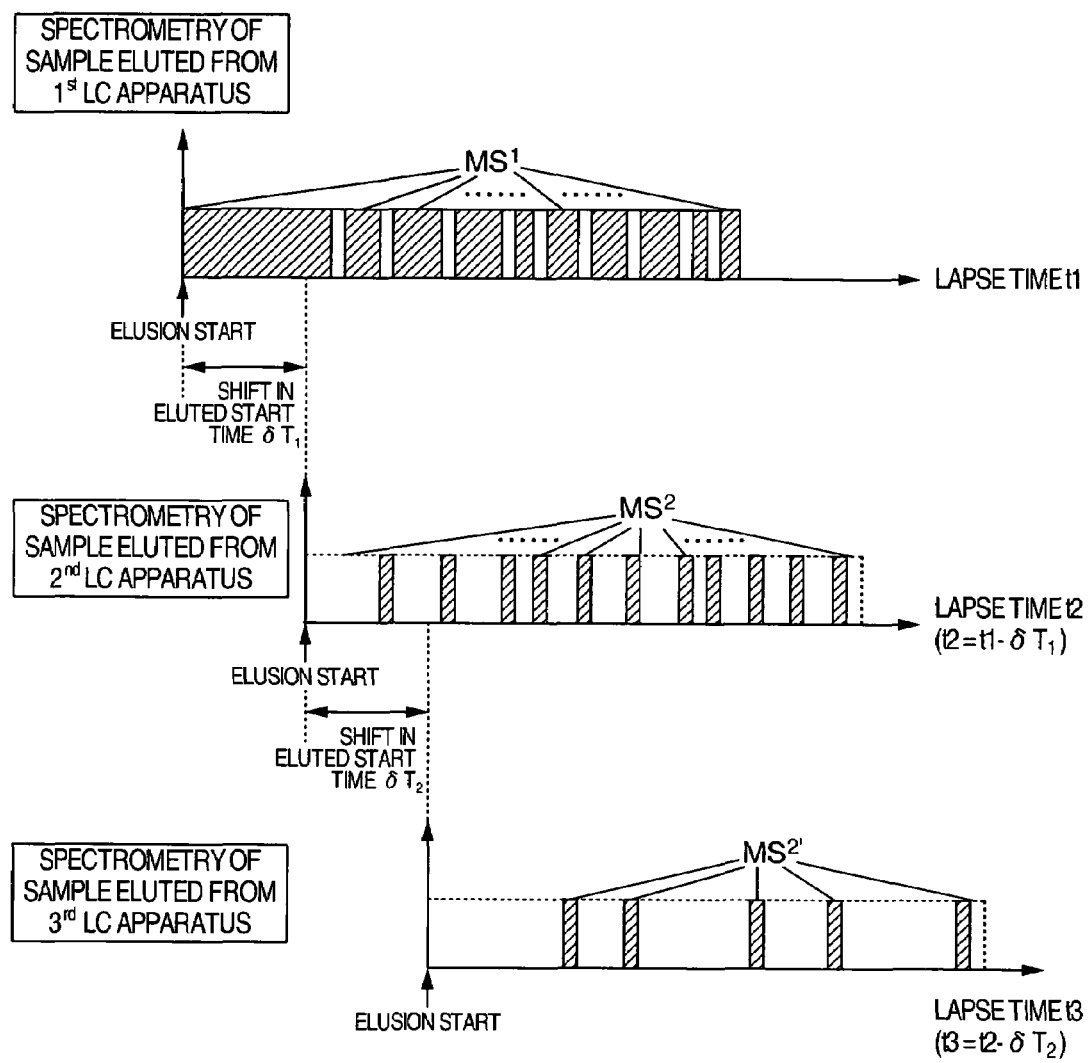

MASS SPECTROMETRIC METHOD AND MASS SPECTROMETRIC SYSTEM

BACKGROUND OF THE INVENTION

The present invention relates to a mass spectrometric method for performing tandem mass spectrometry of a sample separated by a chromatography apparatus and a mass spectrometric system suitable for carrying out the method.

Generally, in a liquid chromatography (LC) apparatus or gas chromatography (GC) apparatus-tandem mass spectrometric system, a sample to be measured is temporally separated into constituents depending on differences in times for the sample constituents to pass through the LC or GC apparatus. Subsequently, the thus separated sample constituents are ionized and a variety of created ions are sent to a mass spectrometer, in which ionic strengths are measured in respect of individual mass versus (electric) charge ratios m/z each representing a ratio of mass number m to atomicity z of an ion. A mass spectrum obtained from results of the measurement includes peaks of ionic strengths (ionic peaks), measured in respect of the individual mass versus charge ratio m/z values, of sample constituents eluted from the LC or GC apparatus at time points. The mass spectrometry of the ionized sample constituents of their own as above is called $MS^1$. In a tandem type mass spectrometric system capable of performing a multi-stage dissociation operation, an ionic peak of an ion having a specified mass versus charge ratio m/z is selected from ionic peaks detected in the $MS^1$ (the thus selected ionic sort is called a parent ion), the parent ion is dissociated by, in general, causing it to collide with gas molecules to create dissociated ionic sorts and the thus created dissociated ionic sorts are subjected to mass spectrometry to obtain a mass spectrum in a similar way. Here, a process for dissociating the parent ion through n stages and performing mass spectrometry of resulting dissociated ion sorts is called $MS^{n+1}$. As described above, in the tandem type mass spectrometer, a parent ion is dissociated through multiple stages (first stage, second stage, ..., n-th stage) and mass numbers of ionic sorts created in the respective stages are subjected to mass spectrometric operations ($MS^2$, $MS^3$, ..., $MS^{n+1}$).

(1) In most of the mass spectrometer capable of performing tandem spectrometry, the tandem spectrometry is carried out by the data dependent function in which when selecting parent ions for use in $MS^2$ spectrometry on the basis of $MS^1$ data obtained at individual time points of eluting from the LC or GC, parent ions are chosen in order of ionic peaks of higher strengths (for example, ionic peaks within 10 high-ranking strengths) and subjected to dissociation and mass spectrometry ($MS^2$).

(2) One may refer to JP-A-2002-168842 and a product introduction of a system for ADME/TK, http://www.waters.co.jp/index.html which disclose known examples of a combined system of a plurality of liquid chromatography apparatus and a mass spectrometer.

The former reference is directed to a system for introducing samples to a plurality of columns by switching over valves, thus disclosing an example in which mass spectrometry is conducted by providing different samples with different elusion times in the plural columns and also disclosing an example in which mass spectrometry of the same sample is conducted by changing the separation condition the column has.

The latter reference is also directed to a tandem mass spectrometric system having a plurality of columns and a mass spectrometer in combination, disclosing a system utilizing a time-difference chromatography apparatus which starts chromatography by shifting start time.

Through the data dependent function shown in (1) as above, ions are selected in order of high-ranking strengths in $MS^1$ data at current time regardless of $MS^1$ data obtained before and after each elusion time and consequently, there is a possibility that either an ion of high strength kept to be eluted for a fairy long time or an ion eluted at a time point at which the ionic strength is not near a peak will be selected and ionic strength is not near a peak will be selected and subjected to $MS^2$ spectrometry. In the former case, the same ion is taken as an object of $MS^2$ many times for a fairy long time and in the latter case, the ionic strength deviating from the peak is responsible for reduction of strength of $MS^2$ data itself, giving rise to the occurrence of inefficient tandem mass spectrometry.

The system disclosed in JP-A-2002-168842 intends to provide how to acquire many sorts of $MS^1$ data, failing to presuppose any tandem mass spectrometry. The latter reference shows the tandem mass spectrometric system utilizing the time-difference chromatography apparatus which starts spectrometry by shifting start time but it does not refer to exchange of chromatogram data and mass spectrometry data among a plurality of columns, so that, in the mass spectrometer, $MS^2$ spectrometry is conceivably carried out under the same spectrometry condition. In such a case, spectrometry can be done with high throughput but the results of $MS^2$ spectrometry do not change with samples from the individual columns and conceivably, the efficiency of tandem spectrometry will not change.

SUMMARY OF THE INVENTION

In the light of the problems encountered in the prior art references, the present invention has for its object to provide a LC/GC apparatus-tandem mass spectrometric system which can carry out tandem spectrometry with high throughput and high efficiency.

According to this invention, a mass spectrometric method is provided in which a plurality of chromatography apparatus arranged in parallel (juxtaposed) and connected to a mass spectrometer start elusion at different time points, a sample eluted from a precedently starting chromatography apparatus is subjected to mass spectrometry by means of the following mass spectrometer capable of performing tandem mass spectrometry, data of chromatogram by the precedently starting chromatography apparatus is analyzed on real time base and on the basis of results of the analysis, a mass spectrometry condition and/or mass spectrometry contents when a sample eluted from a succeeding chromatography apparatus is subjected to mass spectrometry is changed on real time base.

According to this invention, a mass spectrometric system is provided which comprises a plurality of chromatography apparatus having mutually different elusion start times, a tandem mass spectrometer for performing mass spectrometry of a sample separated by the chromatography apparatus and a controller for performing a process of analyzing data of chromatogram obtained from a precedently starting one of the plural chromatography apparatus within a real time during measurement and commanding, on the basis of results of the analysis process, that a mass spectrometry condition and/or mass spectrometry contents when a sample eluted from another chromatography apparatus is subjected to mass spectrometry to be changed on real time base.

According to this invention, a tandem mass spectrometric system is provided which can perform tandem spectrometry of a sample separated by a chromatography apparatus with high efficiency and high throughput.

With the object of solving the above problems in a mass spectrometric system capable of performing tandem spectrometry, an embodiment of the present invention is concerned with a system which adopts the following means (A) and (B) to analyze, at a high speed within a real time of measurement, a mass spectrum ($MS^n$) obtained by dissociating a target ion (n−1) times and subjecting it to mass spectrometry to thereby decide the following spectrometry contents.

(A) In a tandem mass spectrometric system having a plurality of LC or GC apparatus whose elusion start times are shifted from each other by a predetermined amount, chromatogram data and mass spectrometry data of a precedently starting LC or GC apparatus are analyzed within a real time of measurement and on the basis of results of the analysis, a spectrometry condition/spectrometry contents when a sample eluted from a succeeding LC or GC apparatus is subjected to tandem spectrometry is optimized. In other words, the data of the precedently starting LC or GC apparatus is exchanged within the system so as to be utilized when the sample eluted from the successively starting LC or GC apparatus is subjected to tandem spectrometry.

(B) In the above (A), since the analysis of the chromatogram data and mass spectrometric data of the precedently starting LC or GC apparatus within a real time of measurement makes it known, within the real time of measurement, what mass versus charge ratio an ion sort has and at what time point of eluting its ionic strength comes to the proximity of a peak, the ion sort having its ionic strength near the peak can be selected as a target of $MS^2$.

Examples of system construction conceivable in the present invention will be enumerated in the following.

(1) In a system in which a sample to be subjected to mass spectrometry is passed through a plurality of juxtaposed chromatography apparatus, the sample is separated into constituents in accordance with holding time points during passage of the sample through the chromatography apparatus and the sample constituents are ionized in an ionizing unit to create various sorts of ions which in turn are subjected to mass spectrometry in a mass spectrometer, data of chromatogram obtained in one of the juxtaposed plural chromatography apparatus is processed within a real time during measurement and on the basis of results of the process, a mass spectrometry condition and/or mass spectrometry contents when a sample eluted from another chromatography apparatus is subjected to mass spectrometry is changed/adjusted automatically.

(2) In the mass spectrometric system as above, the plural juxtaposed chromatography apparatus are a plurality of liquid chromatography (LC) apparatus arranged in parallel.

(3) In the mass spectrometric system as above, the plural juxtaposed chromatography apparatus are a plurality of gas chromatography (GC) apparatus arranged in parallel.

(4) The mass spectrometric system as above further comprises a user interface in which a user can designate whether the function of automatically changing and adjusting the mass spectrometry condition and/or mass spectrometry contents is to be executed or not when data of chromatogram obtained in one of the plural juxtaposed chromatography apparatus is processed within a real time during measurement and a sample eluted from another chromatography apparatus is subjected to mass spectrometry on the basis of results of the process.

(5) The mass spectrometric system as above further comprises a user interface which enables a user to designate specifications and parameters concerning the function of automatically changing and adjusting the mass spectrometry condition and/or mass spectrometry contents when data of chromatogram obtained in one of the plural juxtaposed chromatography apparatuses is processed within a real time during measurement and a sample eluted from another chromatography apparatus is subjected to mass spectrometry on the basis of results of the process.

(6) In the mass spectrometric system as above, the data of chromatogram obtained in one chromatography apparatus signifies data indicating strengths of ions of sample constituents detected at times (holding times) required for the sample constituents to pass through the one chromatography apparatus.

(7) In the mass spectrometric system as above, the data of chromatogram obtained in one chromatography apparatus signifies data indicating strengths of ions of sample constituents detected at times (holding times) required for the sample constituents to pass through the one chromatography apparatus and determined in respect of individual mass versus charge values m/z of the ions.

(8) In the mass spectrometric system as above in which the mass spectrometry condition and/or mass spectrometry contents is changed/adjusted automatically when data obtained from one of the plural juxtaposed chromatography apparatus is processed within a real time during measurement and a sample eluted from a different chromatography apparatus is subjected to mass spectrometry on the basis of results of the process, the one chromatography apparatus has a time for the sample to start passing (elusion start time) which is earlier than that of the different chromatography apparatus.

(9) In the mass spectrometric system as above in which a time for the sample to start passing (elusion start time) in the one chromatography apparatus is set to be earlier than that in the different chromatography apparatus, the elusion start time in the one chromatography apparatus is made to be earlier than that in the different chromatography apparatus by approximately several minutes to several of tens of minutes.

(10) In the mass spectrometric system as above, the mass spectrometric unit for carrying out mass spectrometry has the function of selecting an ion sort having a specified mass versus charge ration m/z from various sorts of ions to dissociate it and performing tandem mass spectrometry in which selection, dissociation and measurement of an ion sort to be measured are repeated in multiple stages.

(11) In the mass spectrometric system as above in which data of chromatogram obtained in the one chromatography apparatus indicates strengths of ions of sample constituents detected at times (holding times) required for the sample constituents to pass through the one chromatography apparatus, a holding time at which the ion strength is near a peak is calculated within a real time during measurement on the basis of data indicative of detected strengths of ions of sample constituents having passed through the one chromatography apparatus and the mass spectrometric unit selects, for a sample eluted from the different chromatography apparatus, an ion sort having a specified mass versus charge ratio m/z from various sorts of ions to dissociate the ion sort at a time point of holding time which is obtained from the chromatogram data of the one chromatograph apparatus and at which the ion strength is near a and further performs tandem mass spectrometry in which selection, dissociation and measurement of an ion sort to be measured are repeated in multiple stages.

(12) In the mass spectrometric system as above in which data of chromatography apparatus obtained in the one chromatography apparatus indicates strengths of ions of sample constituents detected at times (holding times) required for the sample constituents to pass through the chromatography apparatus and determined in respect of individual mass number versus charge values m/z, a holding time at which the ion strength of an ion having a mass number versus charge value m/z is near a peak is calculated within a real time of measurement on the basis of the data indicative of detected strengths of ions of sample constituents passing through the one chromatography apparatus and determined in respect of individual mass number versus charge values m/z and the mass spectrometric unit selects, for a sample eluted from the different chromatography apparatus, an ion sort having a mass versus charge value m/z to dissociate the ion sort at a time point of holding time which is obtained from the chromatogram data of the one chromatography apparatus and at which the strength of the ion having the mass number versus charge value m/z is near a peak and further performs tandem mass spectrometry in which selection, dissociation and measurement of an ion sort are repeated in multiple stages.

(13) In the mass spectrometric system as above, the timing or time point of holding time at which the ion strength, determined from the chromatogram data of the one chromatography apparatus, is near a peak is within a range of a predetermined time following start of detection of the ion and being more than a time for half-width ($\Delta T$) at the peak of ion strength and less than several times the half-width time.

(14) In the mass spectrometric system as above, the mass spectrometric unit for carrying out mass spectrometry is single and respective samples eluted from the plural chromatography apparatus are switched over so that the samples from the respective chromatography apparatus are alternately subjected to mass spectrometry.

(15) In the mass spectrometric system as above, a plurality of mass spectrometric units for carrying out mass spectrometry are provided and when the chromatography apparatus and the mass spectrometric units are equal in number and correspond to each other in one to one relationship, a sample from each chromatography apparatus flows directly into each mass spectrometric unit so as to be subjected to mass spectrometry and at that time, the spectrometry condition/spectrometry contents of each mass spectrometric unit is changed/adjusted by receiving results of measurement of mass spectrometry by another chromatography apparatus.

(16) In the mass spectrometric system as above, the sample subject to mass spectrometry is a biopolymer related substance such as protein and sugar chain.

(17) In the mass spectrometric system as above, the sample subject to mass spectrometry is a low molecular weight substance such medicines.

(18) In the mass spectrometry system as above in which an ion sort having a specified mass versus charge ratio m/z is selected from various sorts of ions so as to be dissociated and further selection, dissociation and measurement of an ion sort to be measured are repeated in multiple stages, the mass spectrometric unit adopts an ion trap type mass spectrometric unit.

(19) In the mass spectrometric system as above in which an ion sort having a specified mass versus charge ratio m/z is selected from various sorts of ions so as to be dissociated and further selection, dissociation and measurement of an ion sort to be measured are repeated in multiple stages, the mass spectrometric unit adopts an ion trap—time on flight type mass spectrometer.

(20) In the mass spectrometric system as above in which an ion sort having a specified mass versus charge ratio m/z is selected from various sorts of ions so as to be dissociated and further, selection, dissociation and measurement of an ion sort to be measured are repeated in multiple stages, the mass spectrometric unit adopts a quadrupole mass spectrometric unit having a mechanism for selecting an ion of a specified mass versus charge ratio and dissociating it.

(21) In the mass spectrometric system as above in which data of chromatogram obtained in one of a plurality of chromatography apparatus arranged in parallel is processed within a real time during measurement and a sample having passed through a different chromatography apparatus is subjected to tandem mass spectrometry on the basis of results of the process, $MS^1$ spectrometry for performing mass spectrometry without dissociating any sample is applied to the sample having passed through the one chromatography apparatus and $MS^n$ ($n \geq 2$) for performing mass spectrometry by dissociating a sample at least more than once is applied to the sample having passed through the different chromatography apparatus.

(22) In the mass spectrometric system as above in which one of a plurality of chromatography apparatus arranged in parallel has a time for a sample to start passing (elusion start time) which is earlier than that of a different chromatography apparatus and samples having passed through the respective LC apparatus are subjected to tandem mass spectrometry, $MS^1$ spectrometry for performing mass spectrometry without dissociating any sample is applied to a sample having passed through the chromatography apparatus having the earlier elusion start time and $MS^n$ ($n \geq 2$) spectrometry for performing mass spectrometry by dissociating a sample at least more than once is applied to the sample having passed through the chromatography apparatus of the retarded elusion start time.

At least examples as below of the overall construction of a mass spectrometric system according to the present invention will be given.

(a) For a plurality of chromatography apparatus, one tandem type mass spectrometric unit is provided. The juxtaposed chromatography apparatus is connected to the following sample spectrometric unit. Chromatogram data of a preceding one of the plural chromatography apparatus is used for changing and modifying an elusion condition of a succeeding chromatography apparatus.

(b) A plurality of juxtaposed chromatography apparatus are connected to a plurality of juxtaposed mass spectrometric units. In this case, a eluted sample of a preceding chromatography apparatus and a eluted sample of a succeeding chromatography apparatus are subjected to spectrometry at different mass spectrometric units, respectively, and in each channel, chromatogram data of the preceding chromatography apparatus is used for changing and modifying an elusion condition of the succeeding chromatography apparatus. In this case, the sample eluting time is shifted between at least two chromatography apparatus. It will be appreciated that the mass spectrometric unit connected to the preceding chromatography apparatus need not always be a tandem type one.

(c) For a plurality of chromatography apparatus, a chromatogram detector following the preceding chromatography apparatus and a tandem type mass spectrometer following the succeeding chromatography apparatus are arranged.

(d) For a plurality of chromatography apparatus, an ion trap type mass spectrometric unit is provided. In the present specification, the tandem type mass spectrometer is so used as to imply the ion trap type mass spectrometric unit.

(e) For a plurality of chromatography apparatus, an ion trap unit and a time on flight type mass spectrometric unit are provided. In the present specification, the tandem type mass spectrometer is used to imply the use of the ion trap unit and the time on flight type mass spectrometric unit in combination.

(f) For a plurality of chromatography apparatuses a multi-stage Q pole and an ion detector are provided. In the present specification, the tandem type mass spectrometer is used to imply the use of the multi-stage Q pole and the ion detector in combination.

Other objects, features and advantages of the invention will become apparent from the following description of the embodiments of the invention taken in conjunction with the accompanying drawings.

BRIEF DESCRIPTION OF THE DRAWINGS

FIG. 8 is a diagram showing an example of a user interface.

FIG. 9 is a diagram showing another example of the user interface.

FIG. 13A is a time chart schematically showing allotment of times to spectrometric operations of individual LC eluted sample constituents in the fourth embodiment of the invention.

DESCRIPTION OF THE INVENTION

Figure 1:
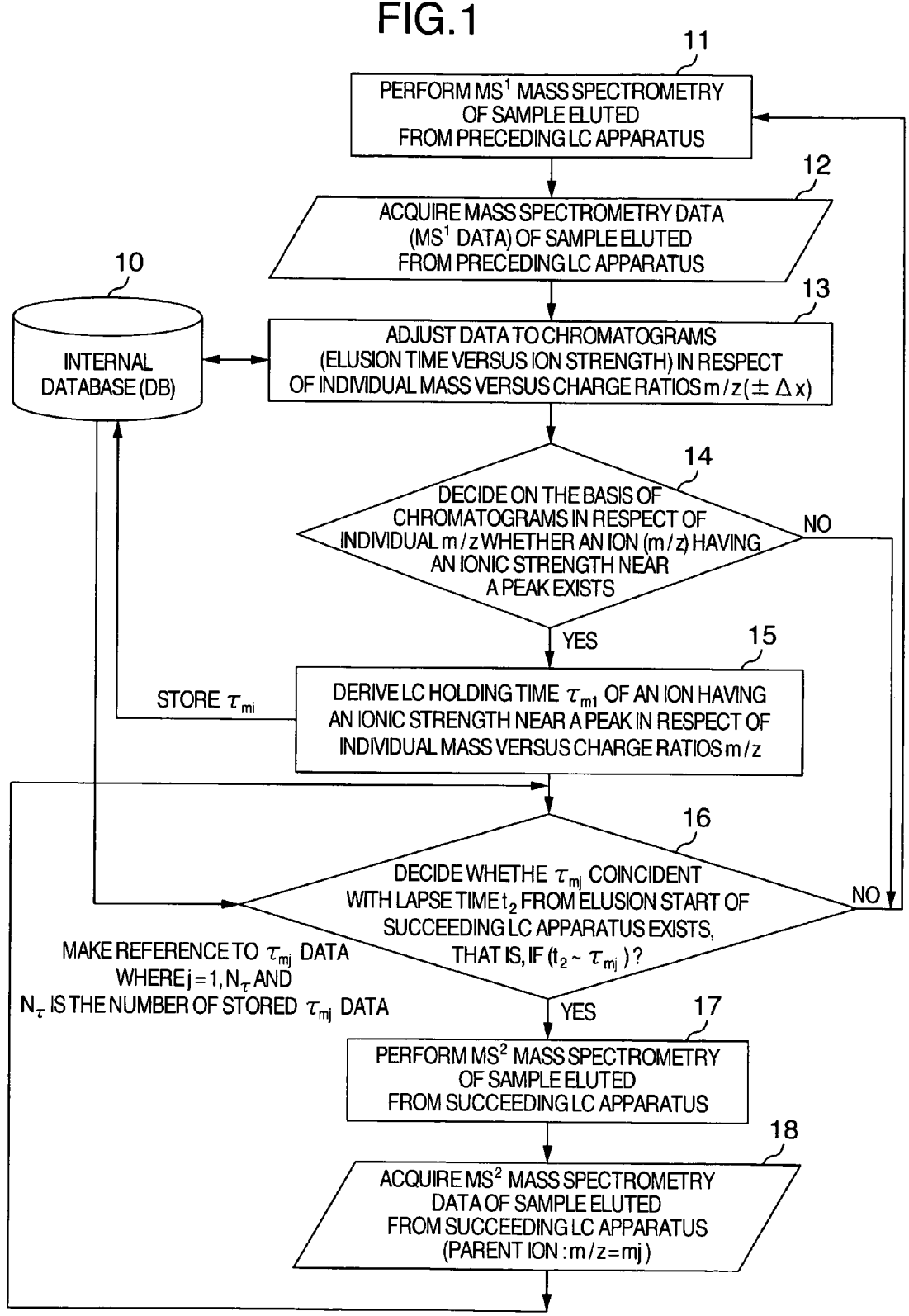
FIG. 1 is a flowchart showing the outline of mass spectrometry according to a first embodiment of the invention.
Figure 2:
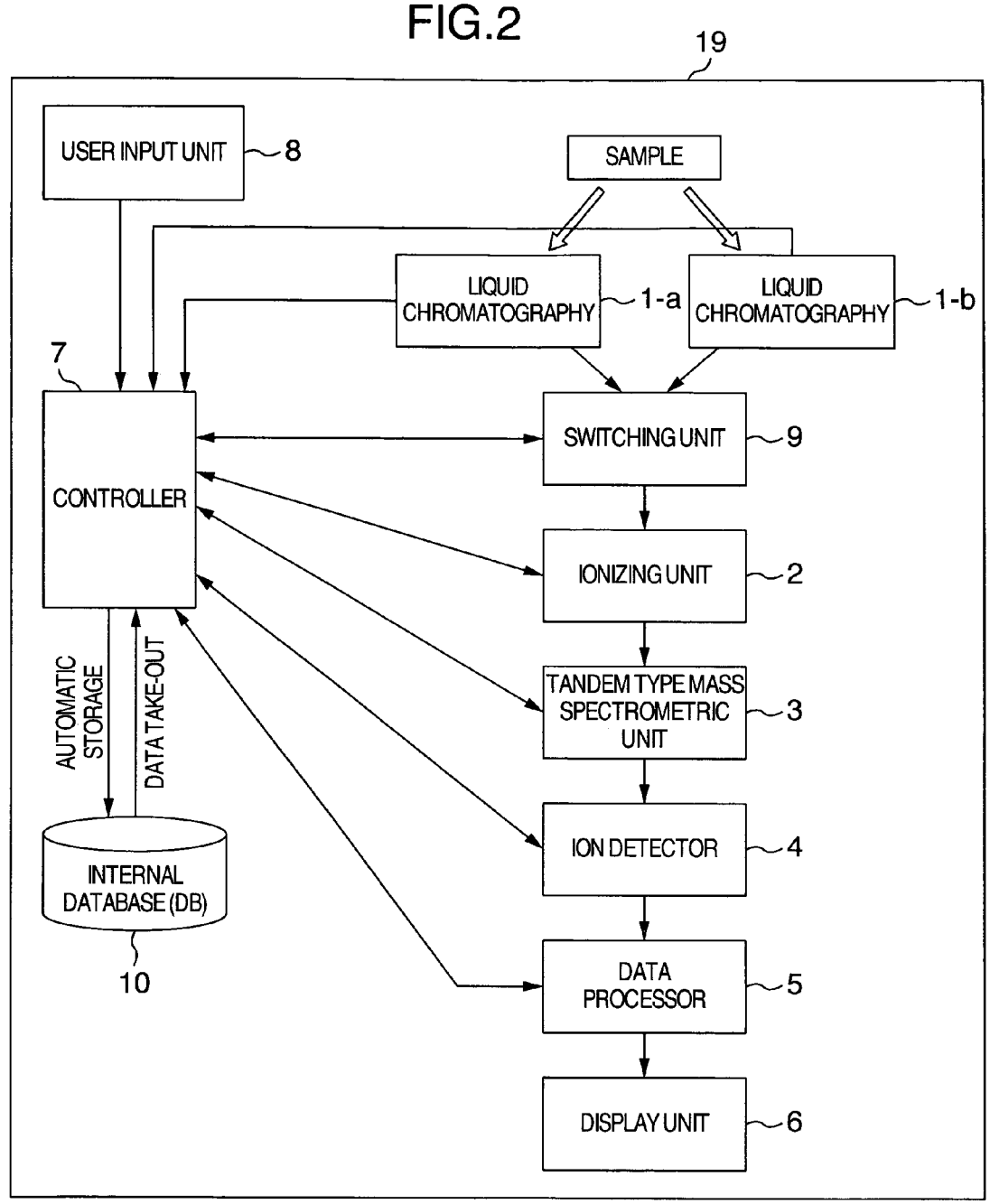
FIG. 2 is a block diagram schematically showing the overall construction of the mass spectrometric system for measuring mass spectrometry data in the first embodiment of the invention.

Embodiments of the present invention will now be described with reference to the accompanying drawings. Firstly, a first embodiment will be described. Illustrated in a flowchart of FIG. 1 is the contents of a process in a mass spectrometric system according to a first embodiment of the invention and illustrated in a block diagram of FIG. 2 is the overall construction of the mass spectrometric system generally designated by reference numeral 19 in the first embodiment. In the mass spectrometric system 19 shown in FIG. 2, a sample to be subjected to mass spectrometry is flown to a liquid chromatography (LC) apparatus 1-a and an LC apparatus 1-b which are juxtaposed or arranged in parallel and is separated and partitioned as time elapses in accordance with difference in adsorption force to columns in the individual LC apparatus. Thereafter, sample constituents eluted from the respective LC apparatus 1-a and 1-b are selected and switched over by means of a switching unit 9 and then ionized in an ionizing unit 2. The thus obtained ions are flown into a tandem type mass spectrometric unit 3 having the function of tandem mass spectrometry. Instead of the LC apparatus, a system utilizing gas chromatography (GC) apparatus may be involved. The sample may be either a biopolymer system substance such as protein and sugar chain or a low molecular weight substance such medicines.

Defined by the tandem mass spectrometric function is the function to select a specified sample constituent ion (parent ion) according to its mass and perform mass spectrometry of dissociated ions created by dissociating the parent ion. In other words, mass spectrometric distribution of sample constituents of substances in an original sample is measured to provide mass spectral data ($MS^1$) and thereafter, a parent ion having a value of m/z is selected and dissociated and obtained dissociated ions are measured to provide mass spectrometry data ($MS^2$). If necessary, the selected precursor ions in the $MS^2$ data are further dissociated and mass spectrometry data ($MS^3$) of obtained dissociated ions is measured so that dissociation and mass spectrometry may be carried out in multiple stages ($MS^n$ ($n \geq 3$). In the present embodiment, the mass spectrometric unit has the spectrometric function up to at least $MS^2$. Indispensably, the mass spectrometer includes the ionizing unit 2, the mass spectrometric unit 3, an ion detector 4 and a data processor 5. A display unit 6 may be incorporated into the mass spectrometer.

For dissociation of the precursor ions, a collision induced dissociation method in which the ions are dissociated by the collision with a buffer gas such as helium will be adopted as will first be described below. For the sake of collision induced dissociation, a neutral gas such as helium gas is needed and therefore a collision cell for collision induced dissociation may be provided separately from the mass spectrometric unit 3 or the mass spectrometric unit 3 may be filled with a neutral gas to cause collision induced dissociation to take place inside the mass spectrometric unit 3. In the latter case, no collision cell is needed. Alternatively, for dissociation, electron capture dissociation may be adopted in which electrons at low energy are irradiated on a target ion to cause it (parent ion) to capture a large amount of low-energy electrons so as to be dissociated.

Turning to FIG. 1, a sample eluted from the preceding LC apparatus undergoes $MS^1$ mass spectrometry in step 11, data of $MS^1$ mass spectrometry of the sample eluted from the preceding LC apparatus is acquired in step 12, the data undergoes a chromatogram process in respect of individual mass versus charge ratios m/z in step 13, the presence or absence of an ion having an ionic strength based on the chromatogram in respect of the individual m/z ratios and coming to the vicinity of a peak is decided in step 14, an LC holding time $\tau_{mi}$ of the ion having the ionic strength, based on the chromatogram in respect of the individual m/z ratios, near the peak is introduced in step 15, the presence or absence of an LC holding time $\tau_{mi}$ of ionic strength peak which coincides with a lapse time from the succeeding LC elusion start is decided in step 16, a sample eluted from the succeeding LC apparatus undergoes $MS^2$ mass spectrometry in step 17 and data of $MS^2$ mass spectrometry of the sample eluted from the succeeding LC apparatus is acquired in step 18.

Through $MS^1$, $MS^2$ and $MS^n$ spectrometric operations in the tandem mass spectrometric unit 3 in FIG. 2, the sample is separated into constituents in accordance with mass-to-charge ratios m/z of their ions. Here, m represents a mass of an ion and z represents an electrification atomicity of the ion. Separated ions are detected by the ion detector 4, applied with data processing and adjustment by the data processor 5 and mass spectrometric data pieces obtained in the steps 12 and 18 and indicative of spectrometry results are displayed on the display unit 6. The whole of a series of mass spectrometric processes, that is, ionization of sample constituents, transfer and inputting of sample ion beams to the mass spectrometric unit 3, mass separation process, ion detection and data process including read of data from a data input unit 8 and write of internal data to a database 10, is controlled by a controller 7. The influence an elusion condition of the preceding chromatography apparatus 1-a has upon the mass spectrometer or spectrometry results are decided from results of analysis by the data processor 5 and by using the results of analysis of the chromatogram data of the preceding apparatus, an elusion condition and/or contents of the succeeding chromatography apparatus 1-b is changed or modified.

A feature of the present invention resides in that shifting of the sample elusion start time by several minutes or several of tens of minutes is set between the LC apparatus 1-a and the LC apparatus 1-b. Here, the LC apparatus 1-a is defined as the "preceding LC apparatus" having an earlier elusion start time and the LC apparatus 1-b is defined as the "succeeding LC apparatus" having a later elusion start time. Under this condition, the process contents in the present embodiment will be described with reference to FIG. 1.

In the mass spectrometric system 19, $MS^1$ mass spectrometry (step 11) of a sample eluted from the "preceding LC apparatus" is carried out and $MS^1$ mass spectrometric data representing the results is obtained (step 12).

Figure 3:
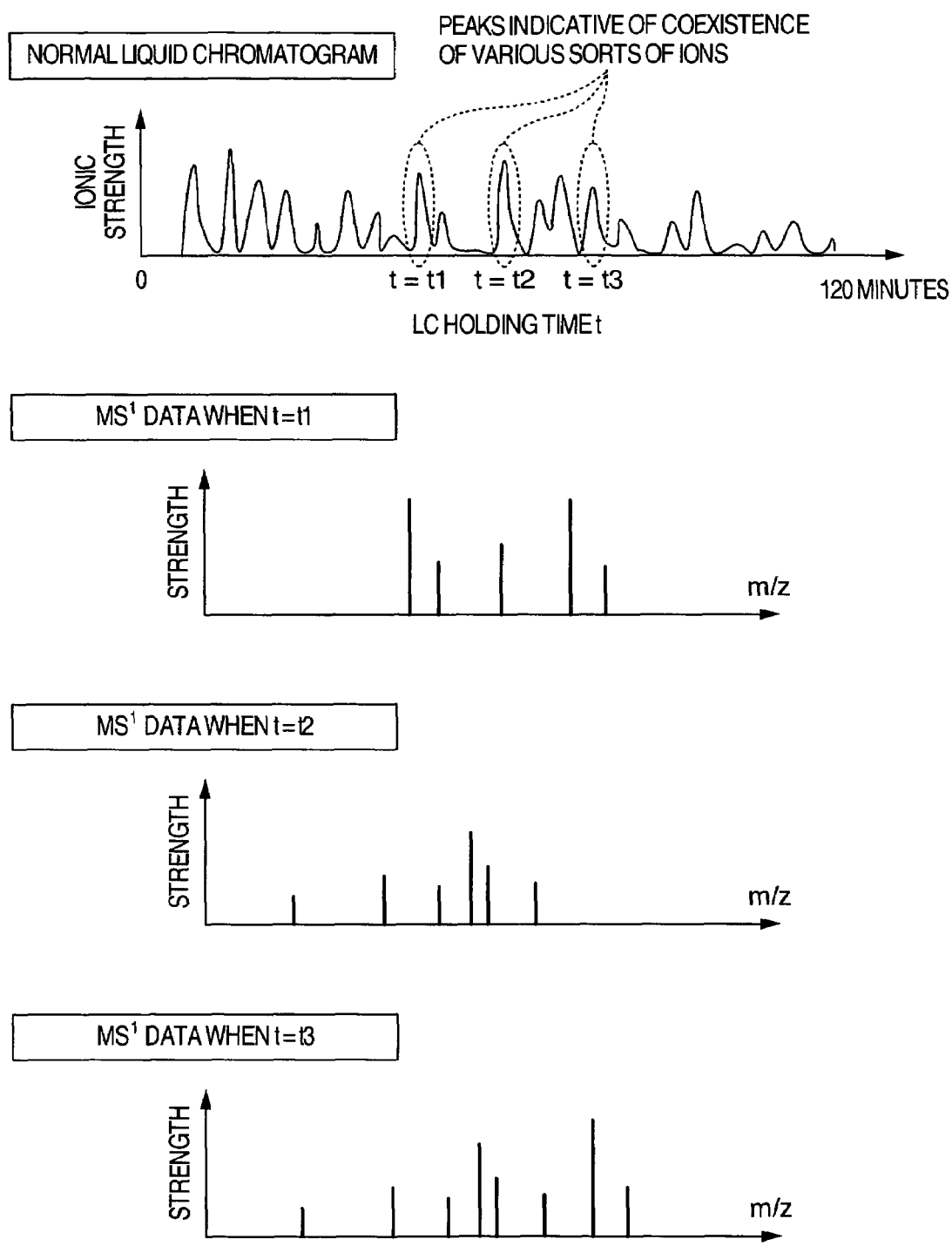
FIG. 3 is a graphical representation showing a normal chromatogram and an example of $MS^1$ mass spectrometry data.
Figure 4:
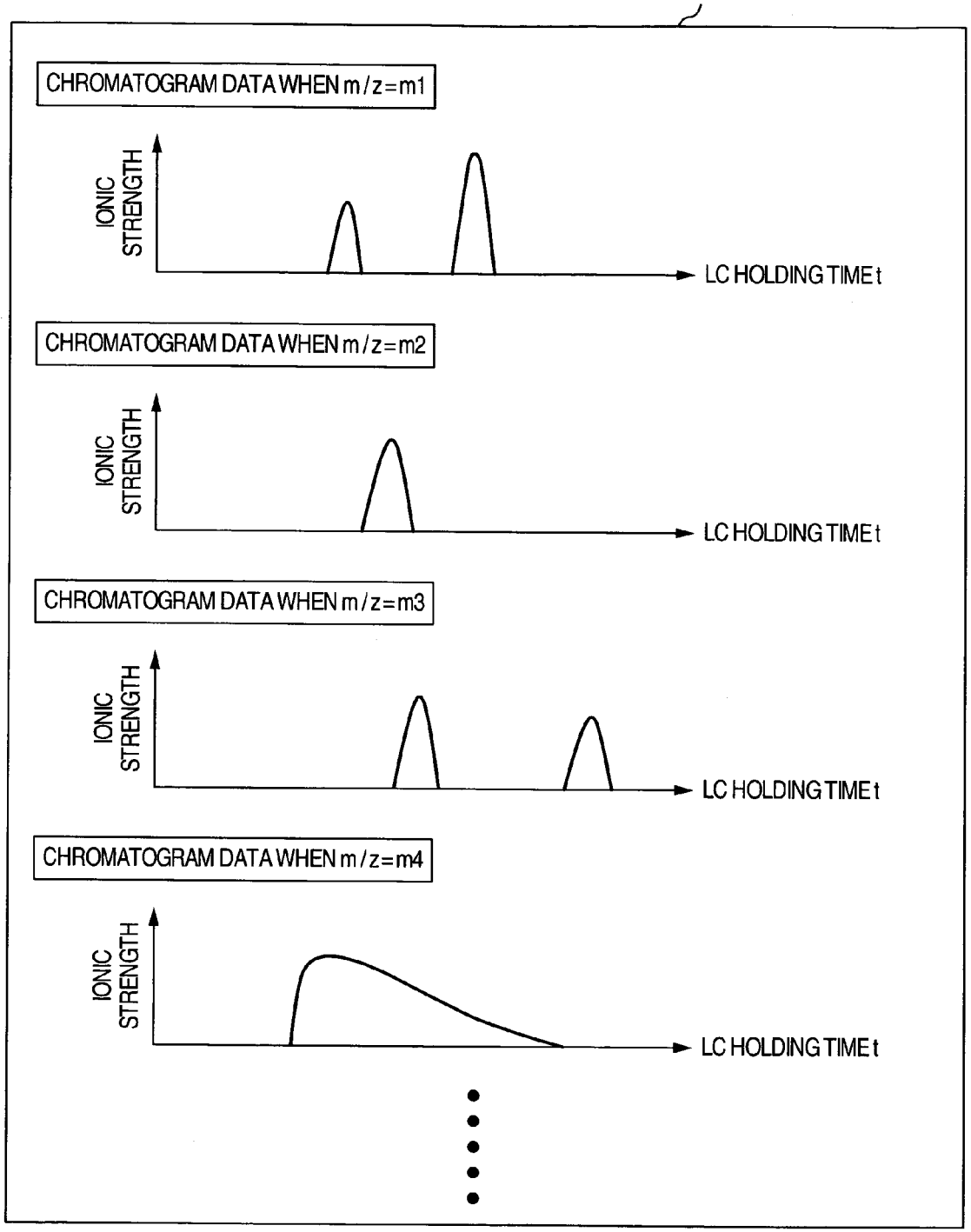
FIG. 4 is a time chart schematically showing the contents of step 13 in FIG. 1 of the invention.

By making reference to FIG. 3, pieces of the $MS^1$ data (step 12) are obtained in respect of individual holding times (elusion times) of the "preceding LC apparatus" 1-a. Then, in the present invention, the pieces of $MS^1$ data in respect of individual holding times (elusion times) of the "preceding LC apparatus" are stored in the internal database 10 included in the mass spectrometric system 19. By consulting pieces of $MS^1$ data in respect of individual holding times (elusion times) of the "preceding LC apparatus" stored earlier than this point of time, chromatograms are adjusted in respect of individual mass versus charge ratios m/z as shown in FIG. 4 where abscissa represents holding time (elusion time) of the "preceding LC apparatus" and ordinate represents ion strength (step 13). In this adjustment, the mass versus charge ratio m/z is permitted to have a margin of $\pm \Delta x$. Preferably, the $\Delta x$ may be changed in accordance with the mass accuracy of the tandem mass spectrometric unit 3.

Figure 5:
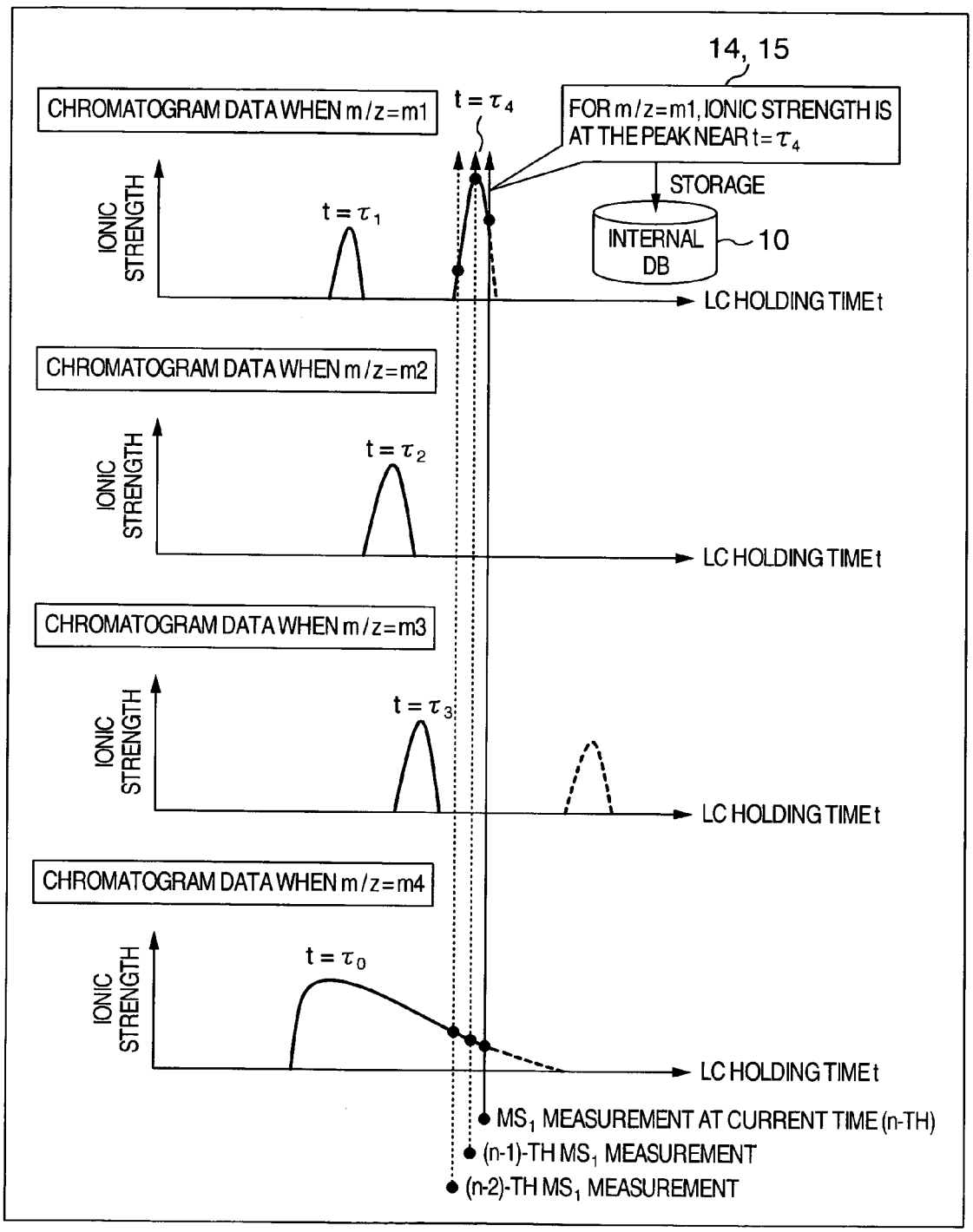
FIG. 5 is a time chart schematically showing the contents of decision 14 and step 15 in FIG. 1 of the invention.

Next, on the basis of the chromatograms in respect of individual mass versus charge ratios m/z as shown in FIG. 4, the present or absence of an ion (m/z) having its ion strength near a peak is searched and determined (step 14). A concrete example will be described with reference to FIG. 5. On the assumption that $MS^1$ measurement operation of a sample eluted from the "preceding LC apparatus" 1-a reaches an n-th measuring point at present, results of chromatographic operations at present in respect of individual mass versus charge ratios m/z are examined to search an m/z coming to an ion peak in comparison with chromatogram in respect of mass versus charge ratio m/z at the previous (n−1)-th measuring point. In the example of FIG. 5, an ion of m/z=m1 has a newly detected peak this time.

In the presence of the ion peak determined in the step 14 as in the example of FIG. 5, a holding time $\tau_{m1}$ of the "preceding LC apparatus" 1-a in the vicinity of the peak of the ion is introduced (step 15) and stored in the internal database 10. Thereafter, the presence or absence of a peak holding time $\tau_{mj}$ coincident with a lapse time t2 from elusion start of the "succeeding LC apparatus" 1-b is searched and determined from peak holding time $\tau_{mj}$ (j=1, $N_\tau$ ($N_\tau$:$\tau_{mj}$ data storing number) (step 16).

In the presence of an ion having a peak holding time $\tau_{mi}$ coincident with the lapse time t2 from elusion start of the "succeeding LC apparatus" 1-b, $MS^2$ mass spectrometry of the sample eluted from the "succeeding LC apparatus" 1-b is carried out in the step 17 and resulting $MS^2$ mass spectrometric data is obtained (step 18). In this case, an ion having $\tau_{mj}$ near an ion peak (m/z=mj) is used as a parent ion to conduct $MS^2$ spectrometry. Subsequently, it is decided whether another ion having $\tau_{mj}$ coincident with the lapse time t2 from elusion start of the "succeeding LC apparatus" 1-*b* is present (step 16) and the steps 16 and 18 are repeated until the absence of a corresponding ion is determined. If in the step 16 the absence of any corresponding ion is settled, the program returns to the process for $MS^1$ mass spectrometry of a sample eluted from the "preceding LC apparatus" 1-*a*.

Accordingly, according to the present embodiment, $MS^2$ mass spectrometry of a sample eluted from the "succeeding LC apparatus" 1-*b* can be conducted near a peak at which a parent ion strength is maximized on the basis of $MS^1$ mass spectrometry of a sample eluted from the "preceding LC apparatus" 1-*a*, so that the quality of $MS^2$ mass spectrometric data can be improved and when a post process of protein identification analysis is carried out by utilizing the data, highly reliable and highly accurate results can be obtained.

Figure 6:
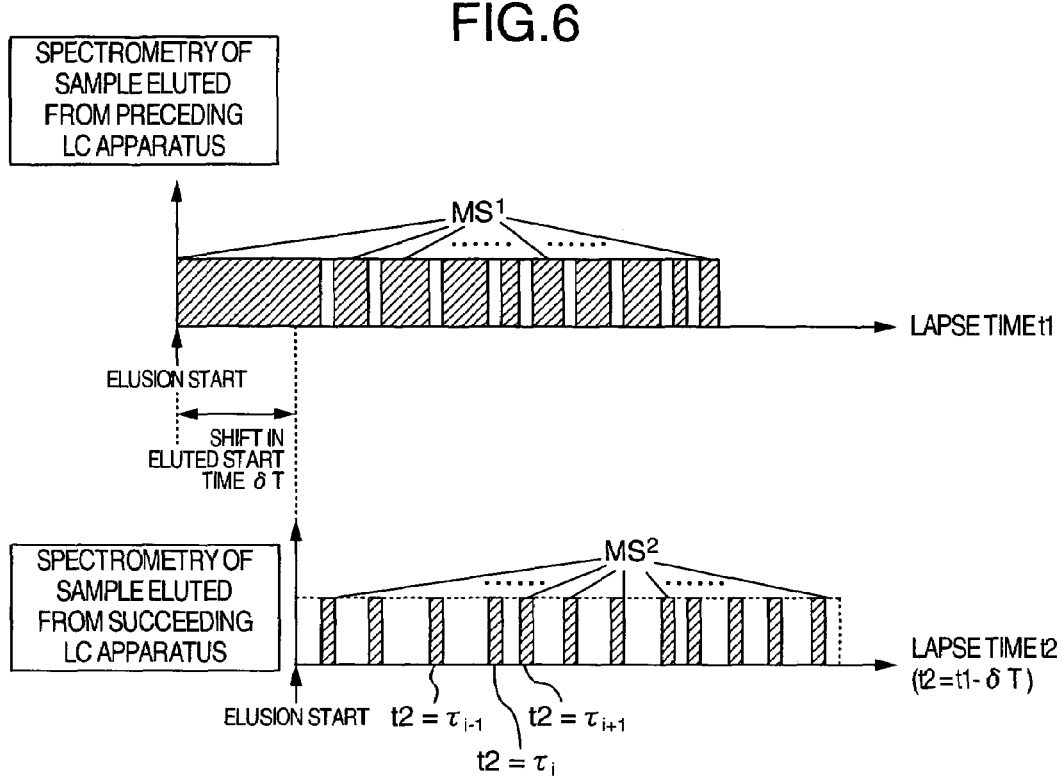
FIG. 6 is a time chart schematically showing allotment of times to spectrometric operations of individual LC eluted sample constituents in the first embodiment of the invention.

Referring now to FIG. 6, an example of allotment of times to $MS^1$ mass spectrometry of a sample eluted from the "preceding LC apparatus" 1-*a* and $MS^2$ mass spectrometry of a sample eluted from the "succeeding LC apparatus" 1-*b* will be described. Here, t1 represents lapse time from elusion start of the "preceding LC apparatus" 1-*a* and t2 represents lapse time from elusion start of the "succeeding LC apparatus" 1-*b*. It will first be appreciated that elusion in the "preceding LC apparatus" 1-*a* is started δT time earlier than that in the "succeeding LC apparatus" 1-*b*. Basically, the sample eluted from the "preceding LC apparatus" 1-*a* is exclusively subjected to $MS^1$ mass spectrometry and the sample eluted from the "succeeding LC apparatus" 1-*b* is exclusively subjected to $MS^2$ mass spectrometry. A timing $t1=\tau_{mi}$ at which an ionic strength an ion sort (m/z=mi) obtained in the $MS^1$ mass spectrometry of the sample eluted from the "preceding LC apparatus" 1-*a* has comes to the vicinity of a peak is stored at any time in the internal database and at a timing at which the holding time t2 of the "succeeding LC apparatus" 1-*b* coincides with $\tau_{mi}$ (timing at which $t1=\tau_{mi}+\delta T$ stands), the sample eluted from the "succeeding LC apparatus" 1-*b* is subjected to $MS^2$ mass spectrometry.

Figure 7:
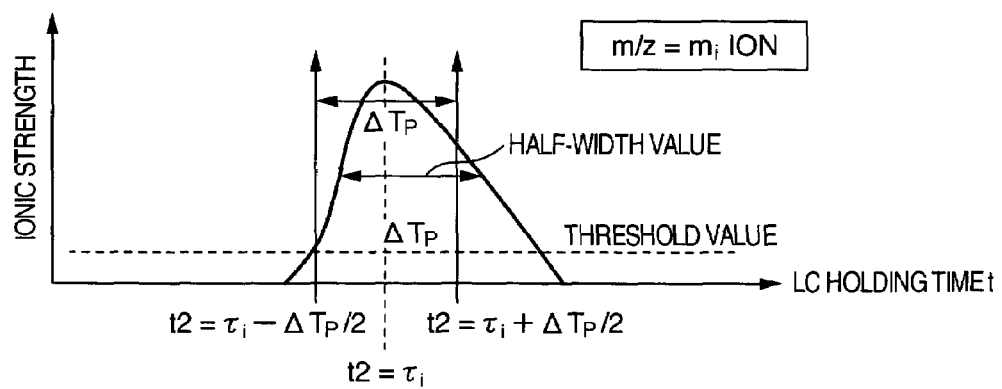
FIG. 7 is a time chart showing an $MS^2$ spectrometry period of each ion sort near a peak on chromatogram.

Further, the number of $MS^2$ mass spectrometry operations of the sample eluted from the "succeeding LC apparatus" 1-*b* at that time will be described with reference to FIG. 7. Preferably, information about a half-width ΔTp of a peak in the chromatogram is also stored in the internal database 10 and during a period that the holding time t2 of the "succeeding LC apparatus" 1-*b* falls in the range of $\tau_{mi}-\Delta Tp/2 \leq t2 \leq \tau_{mi}+\Delta Tp/2$, $MS^2$ mass spectrometry of the sample eluted from the "succeeding LC apparatus" is repeated. This is because there is a possibility that a slight time difference will take place in chromatogram between the "preceding LC apparatus" 1-*a* and the "succeeding LC apparatus" 1-*b* and if $MS^2$ mass spectrometry is carried out at only the timing at which $t2=\tau_{mi}$ stands, malfunction will result. Therefore, for more steadiness, $MS^2$ mass spectrometry may be executed reiteratively during a period of the peak half-width value ΔTp or approximately n times the half-width.

Further, in the present embodiment, it is preferable that an interface be provided which enables a user to select and input through the user input unit 8 a decision made as to whether $MS^1$ spectrometry monitoring based on one LC apparatus and utilizing the difference in elusion start time continues to the execution of the high efficiency spectrometry of $MS^2$ based on the other LC apparatus, as shown in FIG. 8. Further, as shown in FIG. 9, it is preferable to provided an interface which enables the user to decide and input detailed specifications of the system of the invention (for example, the time difference between elusion start times of parallel LC apparatus and the $MS^2$ execution period for peak decision).

In the case of normal LC-MS, in order to know a timing around a peak at which the strength of a parent ion is maximized, the sample must again be eluted from the beginning and subjected to mass spectrometry, with the result that the total measuring time which is twice the total elusion time of the sample (normally, 2 to 3 hours) is required. But according to the present embodiment, by merely increasing the total measuring time by adding approximately +δT (several minutes to several of tens of minutes) to the total elusion time of the sample, $MS^2$ mass spectrometry can be executed near the peak at which the parent ion strength is maximized, so that the quality of $MS^2$ mass spectrometry data can be improved and when a post process of protein identification analysis is carried out by utilizing the data, highly reliable and highly accurate results can be obtained.

Figure 10:
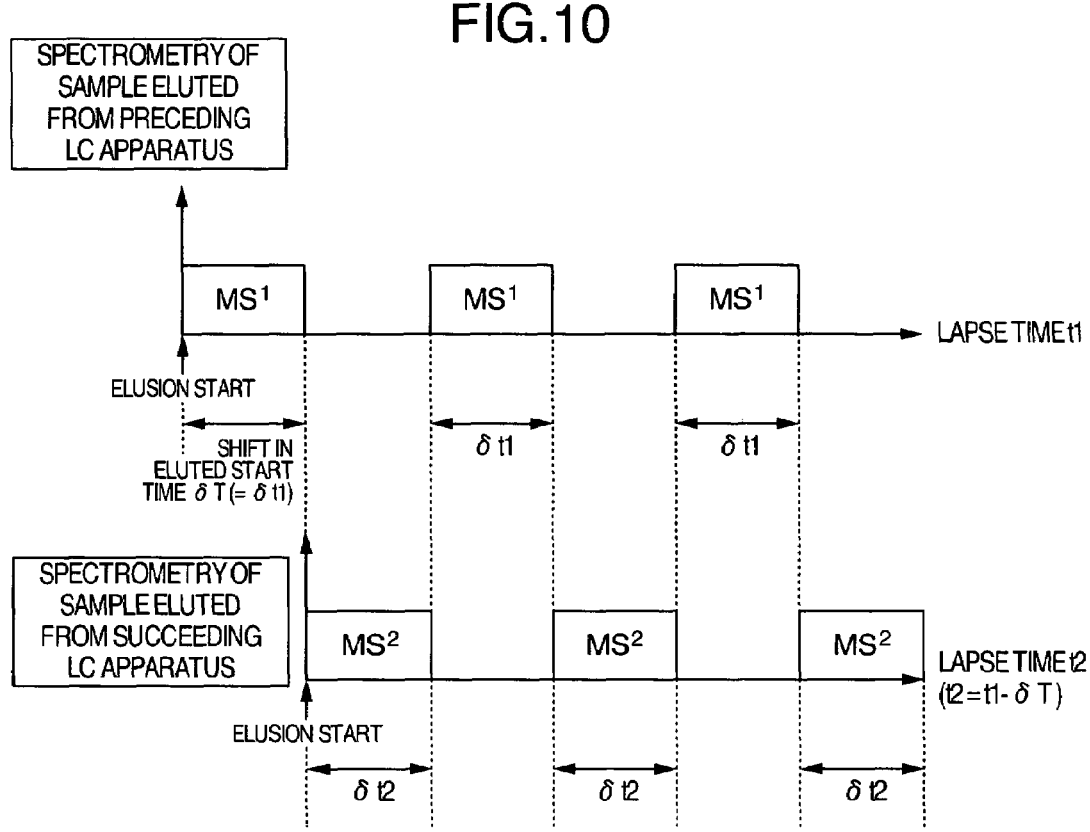
FIG. 10 is a time chart schematically showing allotment of times to spectrometric operations of individual LC eluted sample constituents according to a second embodiment of the invention.

Turning now to FIG. 10, a second embodiment of the invention will be described. In the present embodiment, to exemplify allotment of times to $MS^1$ mass spectrometry of a sample eluted from the "preceding LC apparatus" 1-*a* and allotment of times to $MS^2$ mass spectrometry of a sample eluted from the "succeeding LC apparatus" 1-*b*, predetermined periods are allotted to the $MS^1$ mass spectrometry and the $MS^2$ mass spectrometry, respectively, as shown in FIG. 10. More particularly, a time δt1 (here δt1=δT) is allotted to $MS^1$ mass spectrometry of a sample eluted from the "preceding LC apparatus" 1-*a* and a time δt2 is allotted to $MS^2$ mass spectrometry of a sample eluted from the "succeeding LC apparatus" 1-*b*. In this case, control is very easier than that in embodiment 1 and the present embodiment is suitable for spectrometry of a sample for which chromatogram is known to some extent and a sample having a relatively small number of content substances or constituents.

Figure 11:
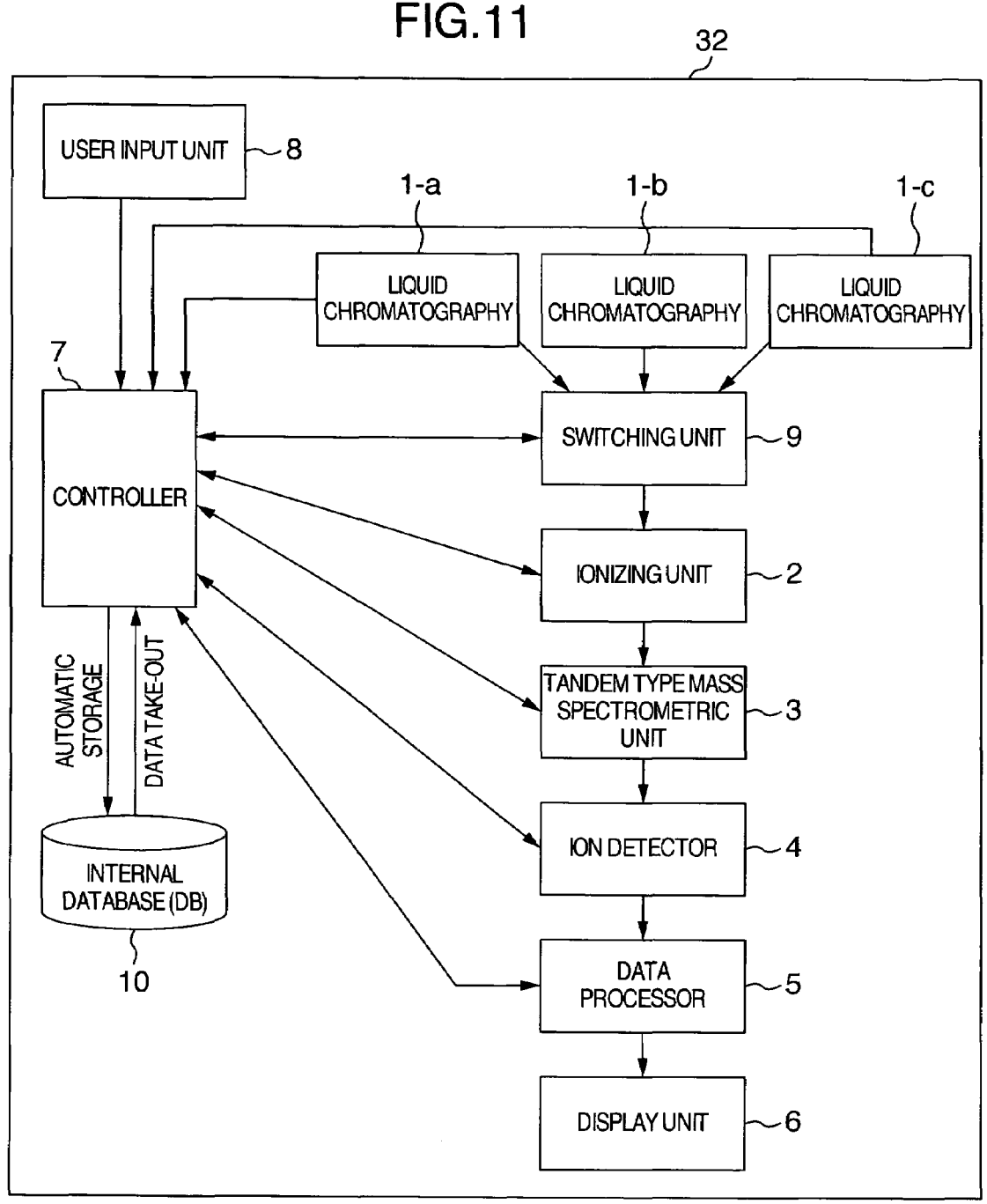
FIG. 11 is a block diagram schematically showing the overall construction of a mass spectrometric system for measuring mass spectrometry data according to third and fourth embodiment of the invention.

Next, a third embodiment of the invention will be described with reference to FIGS. 11, 12A and 12B. The overall construction of a mass spectrometric system shown in FIG. 11 is the same as that in FIG. 1 with the exception that three chromatography apparatus are used and the system is generally designated by reference numeral 32.

In the present embodiment, three LC apparatus 1-*a*, 1-*b* and 1-*c* are used. Here, the LC apparatus 1-*a* is defined as a first LC apparatus having the firstly early eluting start time, the LC apparatus 1-*b* is defined as a second LC apparatus having the secondly early eluting start time and the LC apparatus 1-*c* is defined as a third LC apparatus having the thirdly early eluting start time, thereby shifting the individual elusion start times.

Figure 12A:
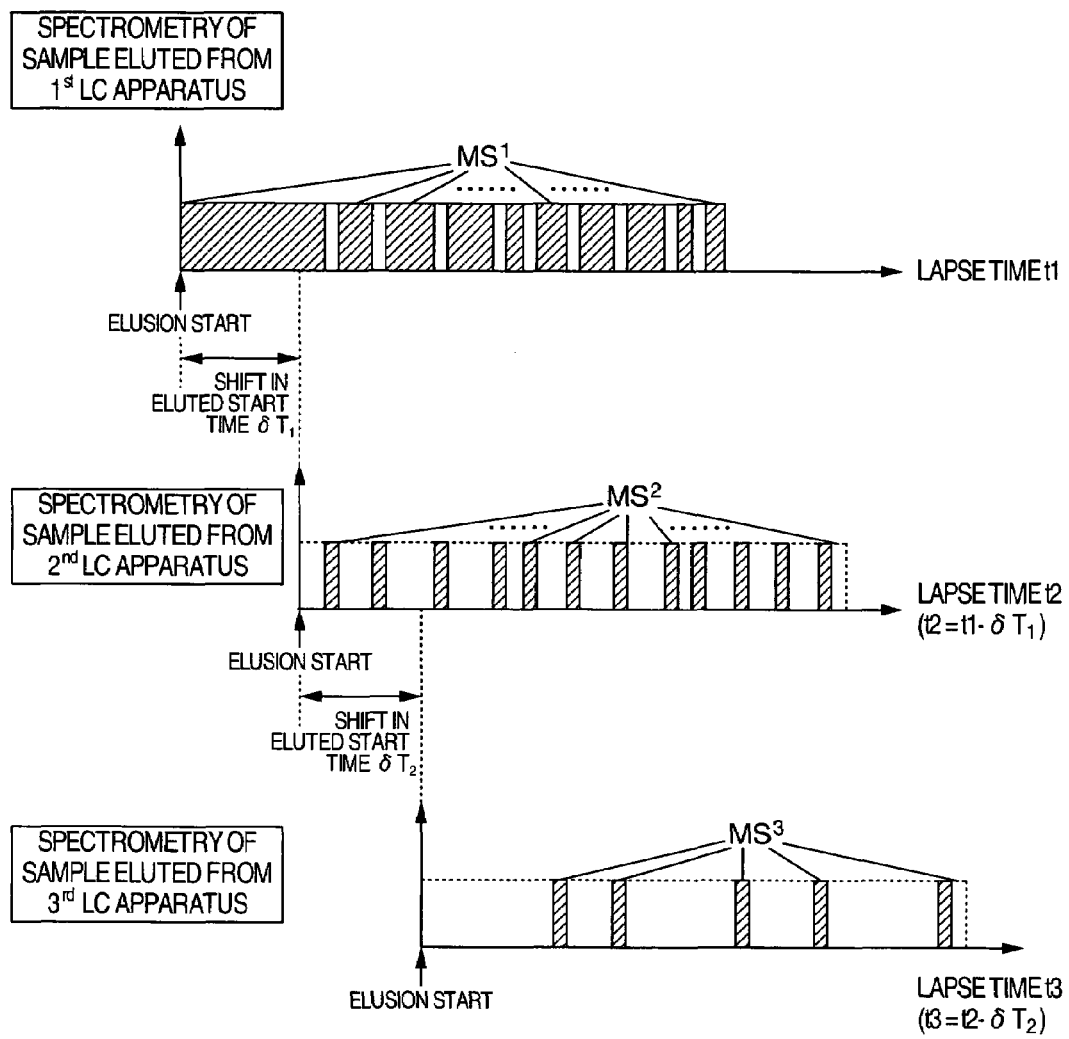
FIG. 12A is a time chart schematically showing allotment of times to spectrometric operations of individual LC eluted sample constituents in the third embodiment of the invention.

Further, when a sample eluted from the "first LC apparatus" 1-*a* is exclusively subjected to $MS^1$ mass spectrometry, a sample eluted from the "second LC apparatus" 1-*b* is exclusively subjected to $MS^2$ mass spectrometry and a sample eluted from the "third LC apparatus" 1-*c* is exclusively subjected to $MS^3$ mass spectrometry, allotment of times to the $MS^1$ mass spectrometry for the sample eluted from the "first LC apparatus" 1-*a*, allotment of times to the $MS^2$ mass spectrometry for the sample eluted from the "second LC apparatus" 1-*b* and allotment of times to the $MS^3$ mass spectrometry for the sample eluted from the "third LC apparatus" 1-*c* are exemplified in FIG. 12A. The contents of time allotment for $MS^1$ mass spectrometry of the sample eluted from the "first LC apparatus" 1-*a* and the contents of time allotment for $MS^2$ mass spectrometry of the sample eluted from the "second LC apparatus" 1-*b* are the same as that explained in connection with FIG. 6.

In $MS^3$ mass spectrometry of a sample eluted from the "third LC apparatus" 1-c, an ion sort (m/z=mi), for which the execution result of $MS^2$ mass spectrometry of the sample eluted from the "second LC apparatus" 1-b determines that the ion sort has a small number of dissociated ions and is not expected to have accuracy of a post process of protein identification, is subjected to $MS^3$ mass spectrometry around a timing $t3=\tau_{mi}$ at which the ionic strength is near a peak, where t3 is lapse time from elusion start of the "third LC apparatus" 1-c, so as to increase the dissociation ion peak, thereby ensuring that the efficiency of tandem mass spectrometry can be expected to be improved.

Figure 12B:
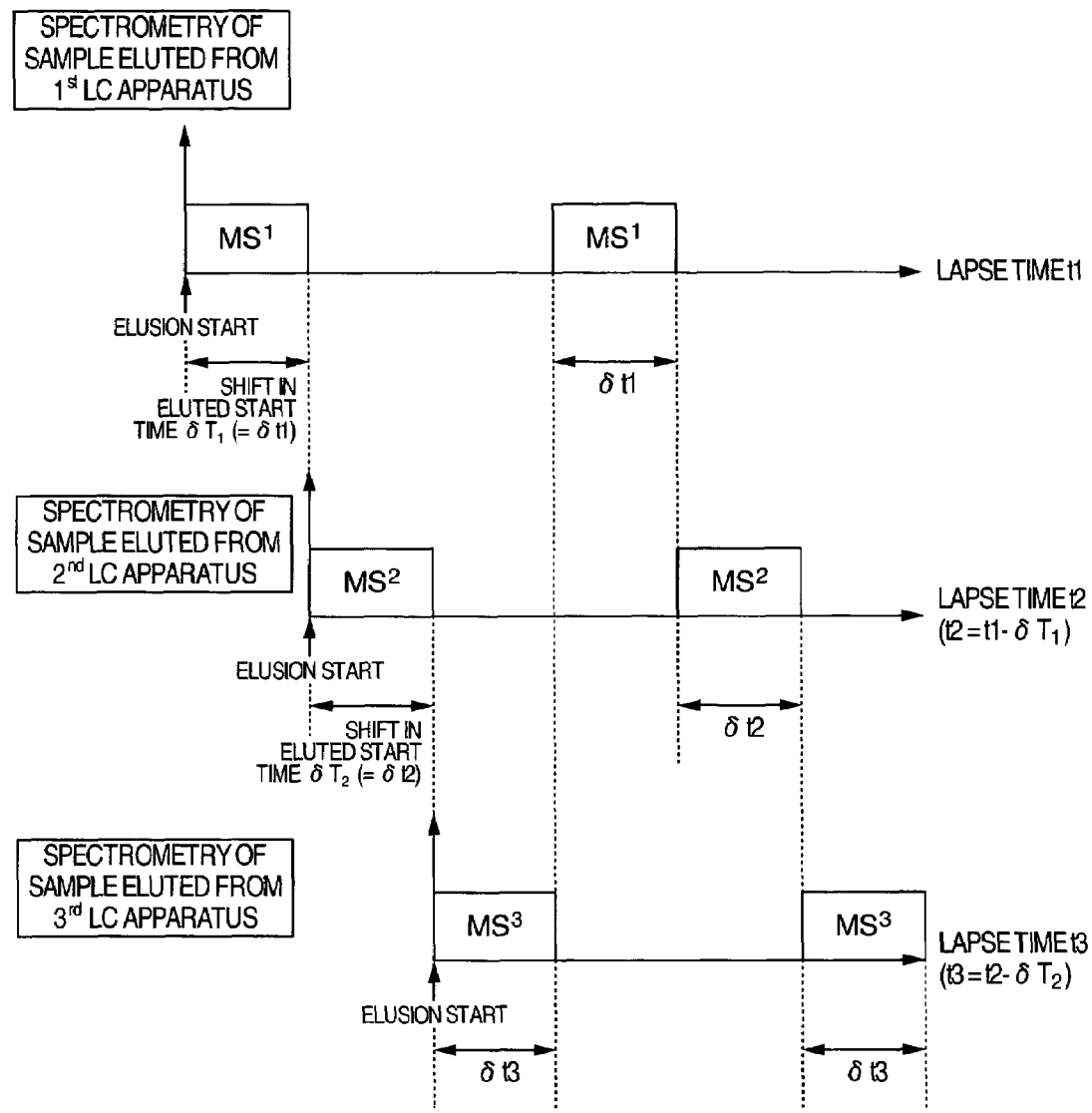
FIG. 12B is a time chart schematically showing allotment of times to individual LC apparatus in the third embodiment of the invention.

In order to facilitate control, $\delta t1$ ($\delta t1=\delta T1$, $\delta t2$ ($\delta t2=\delta T2$) and $\delta t3$ may be set for $MS^1$ mass spectrometry of the sample eluted from the "first LC apparatus" 1-a, $MS^2$ mass spectrometry of the sample eluted from the "second LC apparatus" 1-b and $MS^3$ mass spectrometry of the sample eluted from the "third LC apparatus" 1-c, respectively, as shown in FIG. 12B.

Figure 13B:
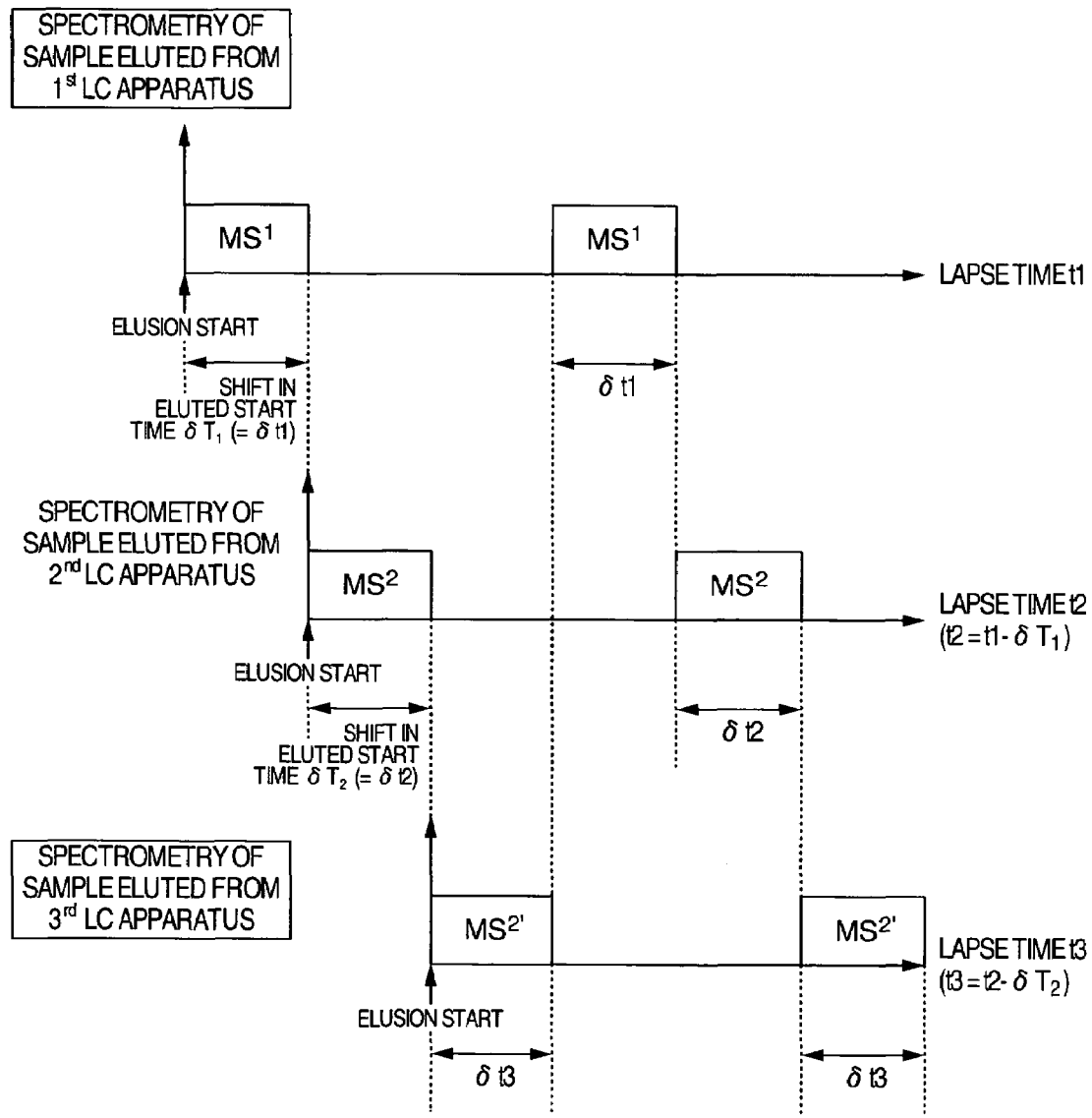
FIG. 13B is a time chart schematically showing allotment of times to individual LC apparatus in the fourth embodiment of the invention.

Referring now to FIGS. 11, 13A and 13B, a fourth embodiment of the invention will be described. The present embodiment is the same as the third embodiment in that the three LC apparatus 1-a, 1-b and 1-c are used as shown in FIG. 11 but it features that a sample eluted from the "third LC apparatus" 1-c is again subjected to $MS^{2'}$ mass spectrometry. In the $MS^{2'}$ mass spectrometry, when the number of dissociated ions is small, an ion having the same mass number m and a different atomicity z is used as a parent ion to again execute the $MS^2$ mass spectrometry. For example, when an ion having m/z≈1001 where m=1000 and z=1 has undergone $MS^2$ mass spectrometry and the number of dissociated ions is determined to be small, $MS^2$ mass spectrometry is again executed using an ion having m/z≈501 where m=1000 and z=2.

Generally, an ion having a larger atomicity z is liable to be dissociated and hence $MS^{2'}$ mass spectrometry is considered to be effective for increasing the number of dissociated ions. In this case, times are allotted to $MS^1$ mass spectrometry of a sample eluted from the "first LC apparatus" 1-a, $MS^2$ mass spectrometry of a sample eluted from the "second LC apparatus" and $MS^{2'}$ mass spectrometry of a sample eluted from the "third LC apparatus", respectively, as exemplified in FIG. 13A.

The allotment of times to the $MS^1$ mass spectrometry of the sample eluted from the "first LC apparatus" 1-a and the $MS^2$ mass spectrometry of the sample eluted from the "second LC apparatus" 1-b is the same as that shown in FIGS. 6 and 12A.

In the $MS^{2'}$ mass spectrometry of the sample eluted from the "third LC apparatus" 1-c, an ion sort (m/z=mi), for which the result of execution of the $MS^2$ mass spectrometry of the sample eluted from the "second LC apparatus" 1-b determines that the number of dissociated ions is small and the accuracy of analysis by a post process such as protein identification is not expected, is subjected to $MS^{2'}$ mass spectrometry around a timing $t3=\tau_{mi}$ at which the ion strength is near a peak, where t3 is lapse time from elusion start of the "third LC apparatus" 1-c, so as to increase the dissociation ion peak, thereby ensuring that the efficiency of tandem mass spectrometry can be expected to be improved.

Here, for the sake of facilitating control, $\delta t1$ ($\delta t1=\delta T1$), $\delta t2$ ($\delta t2=\delta T2$) and $\delta t3$ may be set for the $MS^1$ mass spectrometry of the sample eluted from the "first LC apparatus" 1-a, the $MS^2$ mass spectrometry of the sample eluted from the "second LC apparatus" 1-b and the $MS^{2'}$ mass spectrometry of the sample eluted from the "third LC apparatus" 1-c, respectively, as shown in FIG. 13B.

Figure 14:
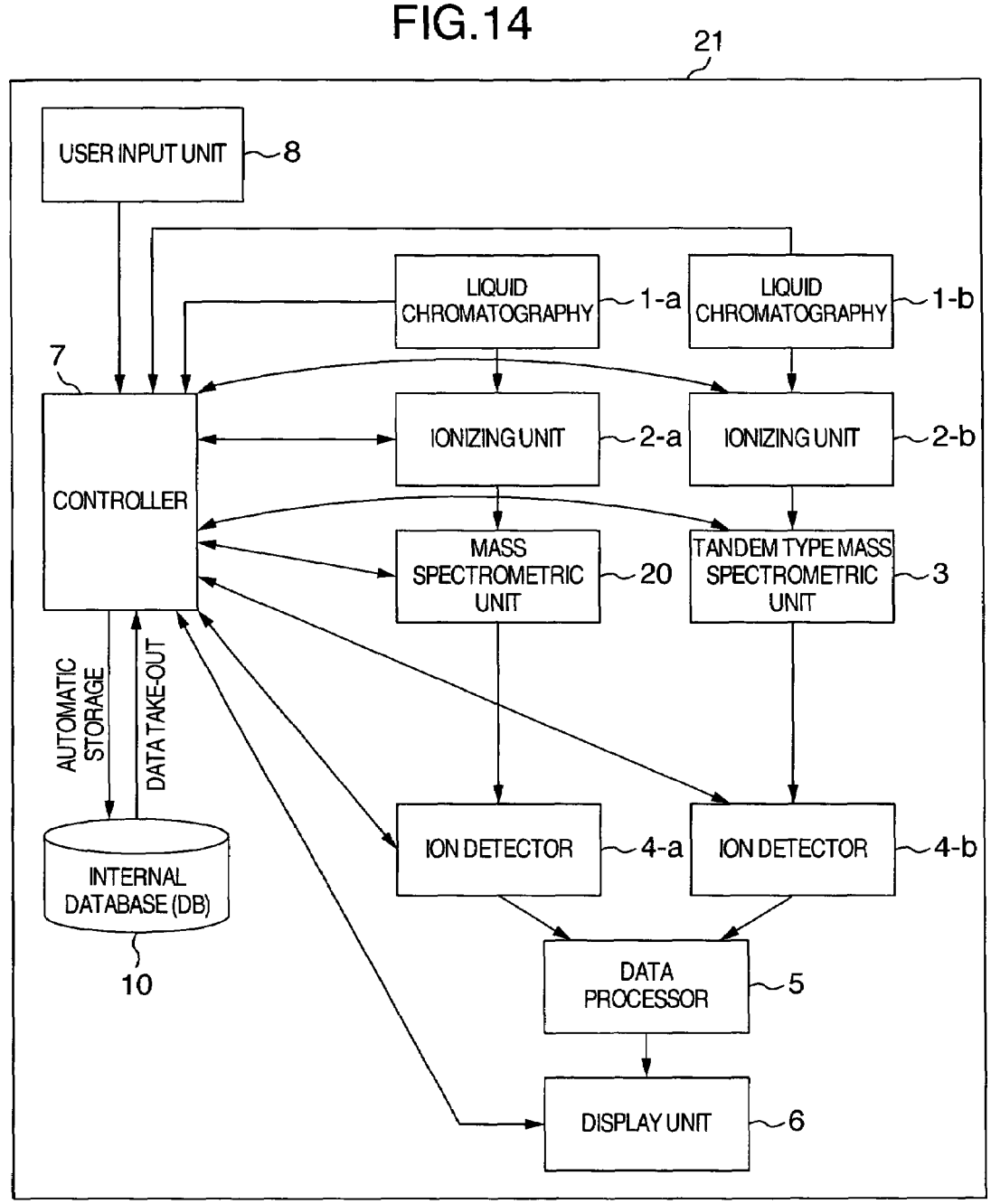
FIG. 14 is a block diagram schematically showing the overall construction of a mass spectrometric system for measuring mass spectrometry data according to a fifth embodiment of the invention.

Turning now to FIG. 14, a fifth embodiment of the invention will be described. In this embodiment, a system 21 includes two channels of LC apparatus 1-a and 1-b, ionizing units 2-a and 2-b, mass spectrometric units 20 and 3 and ion detectors 4-a and 4-b in parallel. But since in the present embodiment, too, a sample eluted from the "preceding LC apparatus" 1-a is exclusively subjected to $MS^1$ mass spectrometry, the mass spectrometric unit 20 for the sample eluted from the "preceding LC" 1-a need not have the tandem mass spectrometry function.

Because of the provision of a plurality of mass spectrometric units, a relatively cheap unit capable of $MS^1$ mass spectrometry may suffice for the mass spectrometric unit 20. In the present embodiment, the two channels of the LC apparatus, ionizing units, mass spectrometric units and ion detectors are provided in parallel and therefore, complicated control for allotment of times to individual spectrometric operations can be unneeded. Further, thanks to the omission of the time allotment, there is no need of providing dead time in the $MS^1$ mass spectrometry and $MS^2$ mass spectrometry. Accordingly, according to the present embodiment, highly effective tandem spectrometry can be executed with high throughput and further reduced wastefulness.

Figure 15:
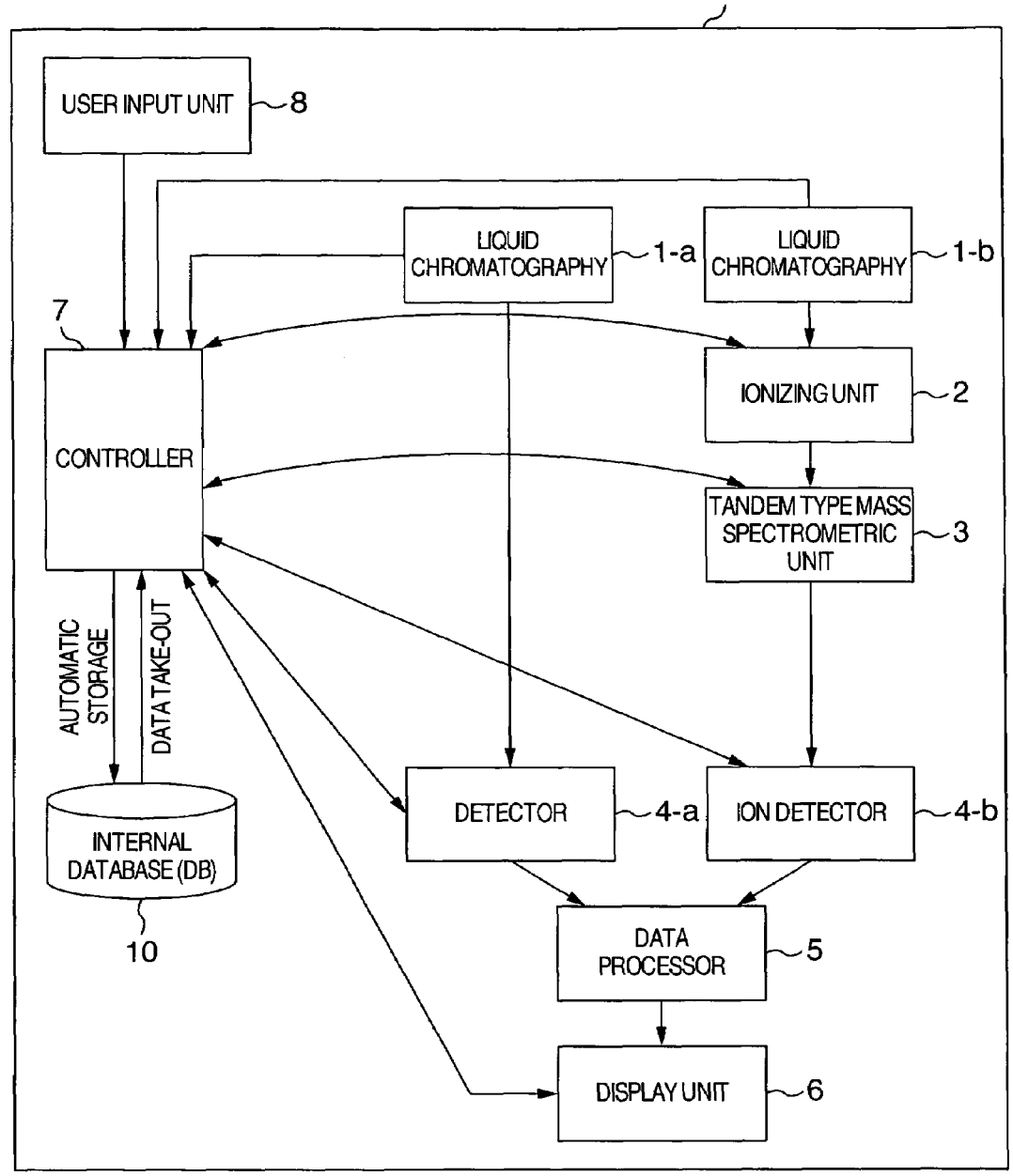
FIG. 15 is a block diagram schematically showing the overall construction of a mass spectrometric system for measuring mass spectrometry data according to a sixth embodiment of the invention.

Next, a sixth embodiment of the invention will be described with reference to FIG. 15. In FIG. 15, the overall construction of a mass spectrometric system is generally designated by reference numeral 22. Here, a sample eluted from the "preceding LC apparatus" 1-a is not subjected to mass spectrometry but is applied to a detector so that normal chromatogram may be detected. At that time, on the basis of chromatogram data obtained from the "preceding LC apparatus" 1-a, a timing of $MS^2$ mass spectrometry of a sample eluted from the "succeeding LC apparatus" 1-b is introduced. In the present embodiment, the chromatogram data obtained from the "preceding LC apparatus" 1-a does not include any mass number data but when either a sample of which the $MS^1$ data mass number is known to some extent or a sample including a small number of ion sorts is to be subjected to spectrometry, the present embodiment does not require any complicated control mechanism and therefore can provide an inexpensive and suitable system.

Figure 16:
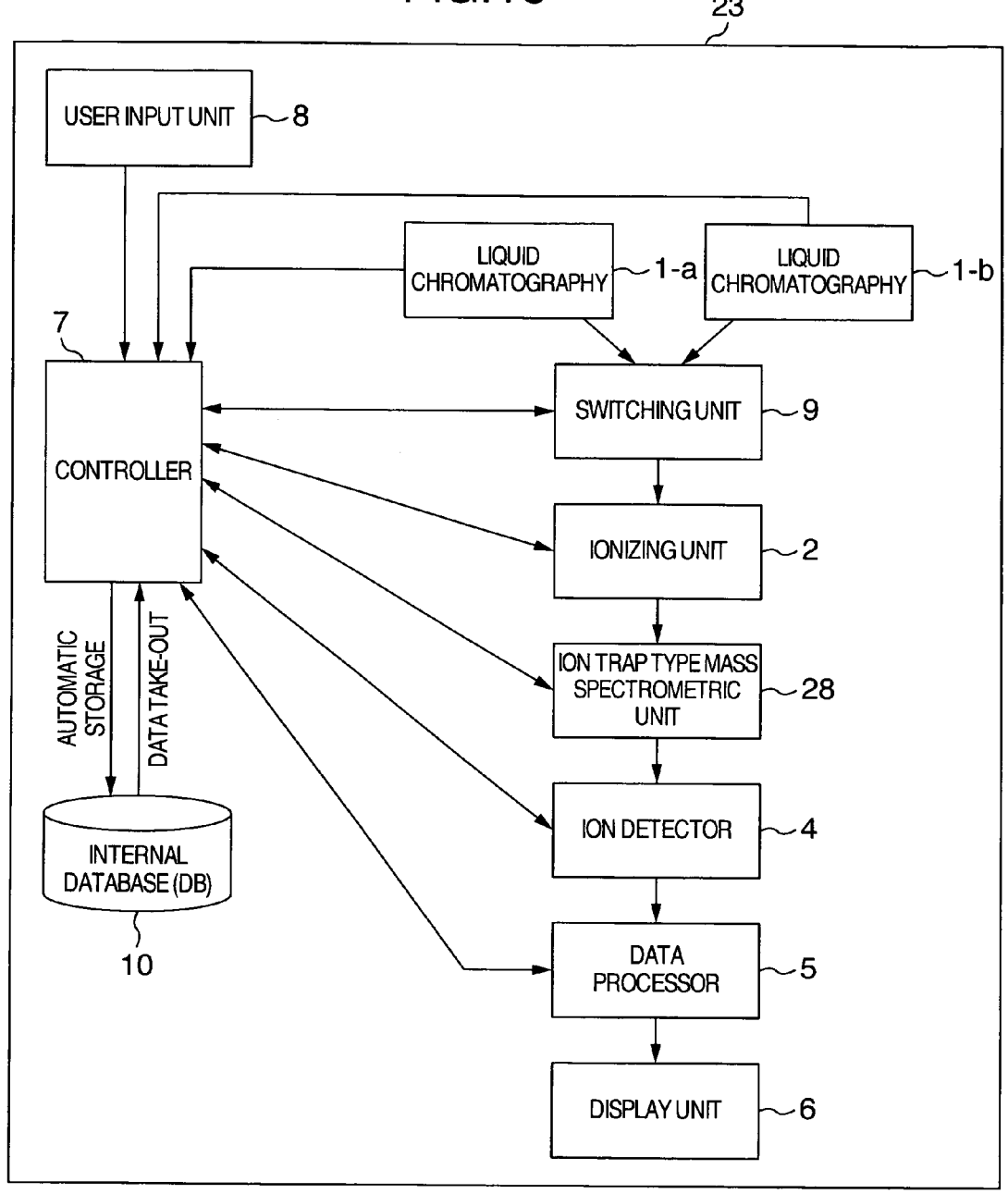
FIG. 16 is a block diagram schematically showing the overall construction of a mass spectrometric system for measuring mass spectrometry data according to a seventh embodiment of the invention.

Next, a seventh embodiment of the invention will be described with reference to FIG. 16. In FIG. 16, the overall construction of a mass spectrometric system is generally designated by reference numeral 23. The present embodiment features that an ion trap type mass spectrometric unit 28 is arranged as tandem type mass spectrometric unit. In this case, an ion trap can play the role of accumulation of ions, selection of parent ion and collision cell and besides can execute mass spectrometry itself and therefore, a space-saving system can be provided.

Figure 17:
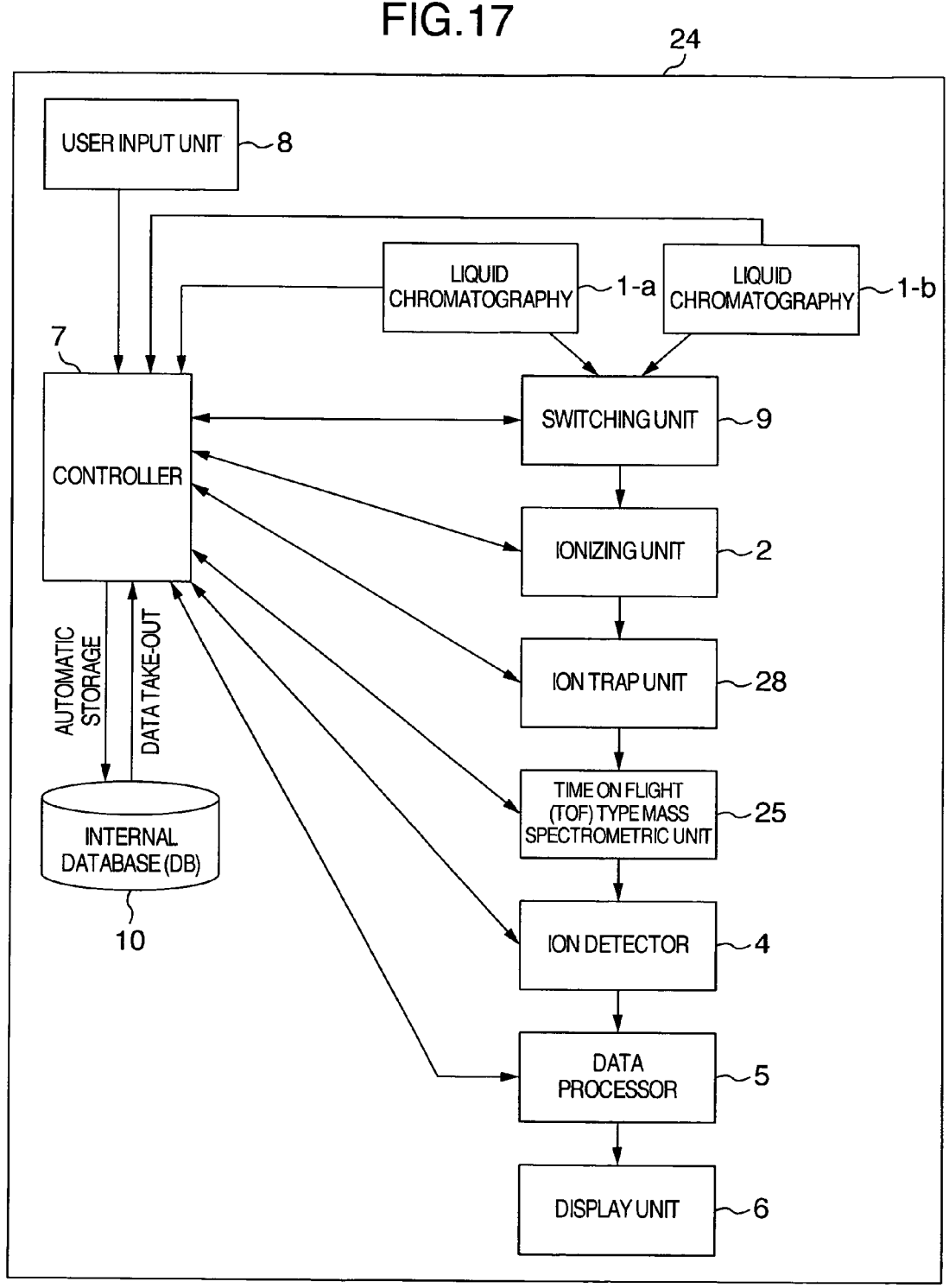
FIG. 17 is a block diagram schematically showing the overall construction of a mass spectrometric system for measuring mass spectrometry data according to an eighth embodiment of the invention.

Next, by making reference to FIG. 17, an eighth embodiment of the invention will be described. In FIG. 17, a mass spectrometric system is generally designated by reference numeral 24. The present embodiment features that an ion trap unit 28—time on flight (TOF) type mass spectrometric unit 25 is arranged as tandem type mass spectrometric unit. In this case, the ion trap is used for accumulation of ions, selection of parent ions and collision cell and for actual mass spectrometry, the TOF unit can perform high-resolution spectrometry. When a sample is a substance of biopolymer system such as protein and sugar chain, the high-resolution spectrometry of large mass number by the TOF can improve the accuracy of a post process such as protein identification analysis and is very versatile.

Figure 18:
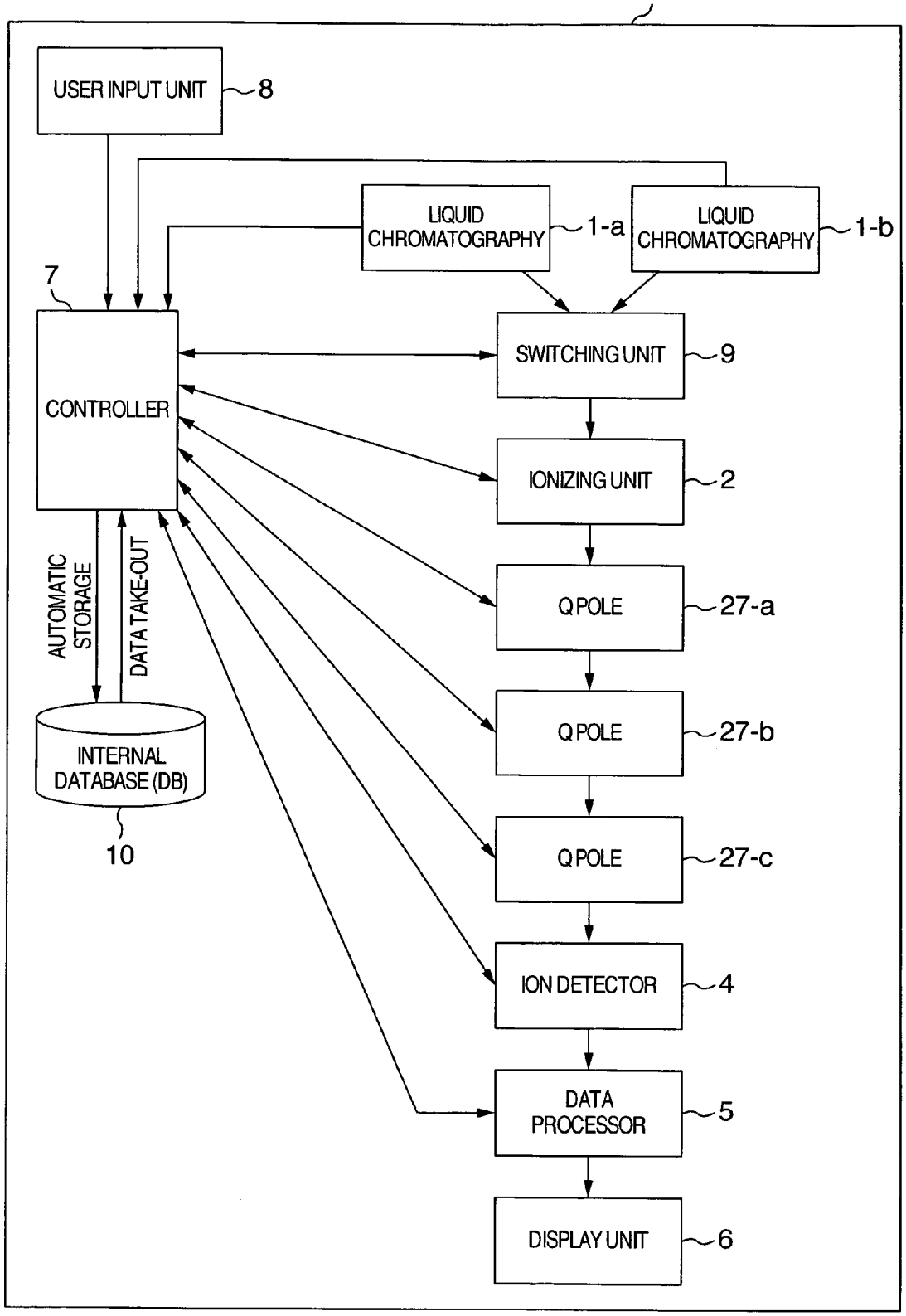
FIG. 18 is a block diagram schematically showing the overall construction of a mass spectrometric system for measuring mass spectrometry data according to a ninth embodiment of the invention.

By making reference to FIG. 18, a ninth embodiment of the invention will now be described with reference to FIG.

18. A system is generally designated by reference numeral 26. The present embodiment features that a mass spectrometric unit having a series of three Q poles (quadruple electrodes) 27-a, 27-b and 27-c is arranged to form a tandem type mass spectrometric unit. In this case, for $MS^1$ mass spectrometry, two of the three Q poles are so controlled as to act as a transportation system and the remaining one is utilized as a mass spectrometric system for the purpose of measuring $MS^1$ mass spectrometric data. For execution of $MS^2$ mass spectrometry, in order to permit only ions subjected to $MS^2$ mass spectrometry to pass on the basis of $MS^1$ mass spectrometric data, voltage of the first Q pole is adjusted, dissociation is attained by collision with a neutral gas filled in the second Q pole, followed by trapping of the thus created dissociated ions, and the dissociated ions are subjected to mass spectrometry in the third Q pole. The tandem mass spectrometric unit based on the three Q poles shown in the present embodiment is a system of positive achievements and advantageously, highly reliable data can be obtained.

Figure 19:
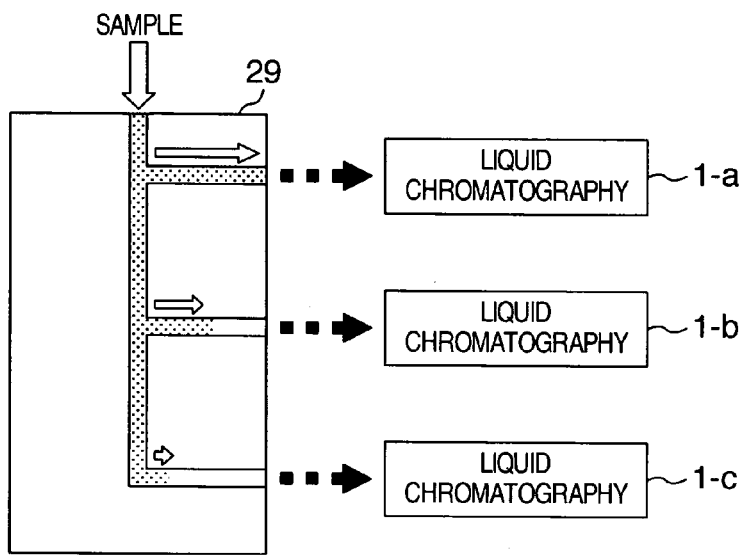
FIG. 19 is a conceptual diagram showing an example of a mechanism for providing differences in elusion start times in a parallel LC system according to a tenth embodiment of the invention.
Figure 20:
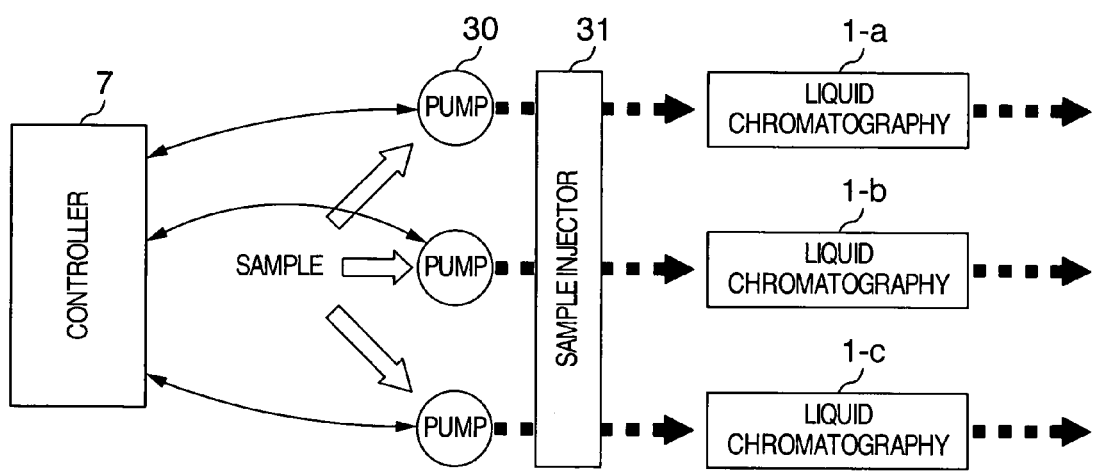
FIG. 20 is a conceptual diagram showing another example of the mechanism for providing differences in elusion start times in the parallel LC system in the tenth embodiment of the invention.

A tenth embodiment of the invention will now be described with reference to FIGS. 19 and 20. The present embodiment is directed to a mechanism for shifting the elusion start times among a plurality of LC apparatus. The mechanism for shifting elusion start times among the plurality of LC apparatus may be constructed in such a way that as shown in FIG. 19, a single flow path extending from a sample is made to branch by means of a distributor 29 and lengths of flow paths ending in entrances of individual LC apparatus are made to be different to provide different times for reaching the entrances, thereby causing the elusion start times to differ. In this case, the elusion start times can be made to be different very cheaply and easily. In an alternative, as shown in FIG. 20, pumps 30 adapted to make inflow of a sample to LC apparatus via a sample injector 31 are controlled temporally by the controller 7 to shift the elusion start time. In this case, a difference in elusion time designated by a user can be reflected stringently and this alternative is preferable for the case where stringency is required.

According to the foregoing embodiments of the present invention, data at an elusion timing near a peak of ionic strength can be obtained from the preceding chromatography apparatus on real time basis by increasing time slightly by about several minutes to several of tens of minutes in terms of the total elusion time and consequently, tandem mass spectrometry can be executed at an elusion timing around a peak of the ion strength, with the result that the quality of tandem mass spectrometric data can be improved and when a post process of protein identification analysis is carried out by utilizing the data, highly reliable and highly accurate results can be obtained.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A method for mass spectrometry in which a plurality of juxtaposed chromatography apparatus connected to a mass spectrometer start elusion at a certain time difference and an elusion sample is subjected to mass spectrometry by means of the following mass spectrometer, wherein chromatogram data obtained from a preceding chromatography apparatus is analyzed on real time base and by using results of the real time analysis of the data by said preceding chromatography apparatus, a mass spectrometry condition and/or mass spectrometry contents when a sample eluted from a succeeding chromatography apparatus is subjected to mass spectrometry is changed on real time base.

2. A mass spectrometric method according to claim 1, wherein results of spectrometry by said mass spectrometer are analyzed and on the basis of the analysis results, a mass spectrometry condition and/or mass spectrometry contents when the sample eluted from said succeeding chromatography apparatus is subjected to mass spectrometry is changed.

3. A mass spectrometric method according to claim 1, wherein said chromatography data is data indicating strengths of ions of sample constituents detected at times required for the sample constituents to pass through said chromatography apparatus.

4. A mass spectrometric method according to claim 1, wherein said chromatography data is data indicating strengths of ions of sample constituents detected at times required for the sample constituents to pass through said chromatography apparatus and determined in respect of individual mass versus charge ratio values m/z of the ions.

5. A mass spectrometric method according to claim 1, wherein said mass spectrometer has the tandem mass spectrometry function of selecting an ion sort having a specified mass versus charge ratio m/z from various sorts of ions to dissociate the ion sort and repeating selection, dissociation and measurement of an ion sort to be measured in multiple stages.

6. A mass spectrometric method according to claim 1, wherein samples eluted to the individual chromatography apparatus are of the same kind and separation conditions by columns of chromatography are the same for the individual samples.

7. A mass spectrometric method according to claim 1, wherein for a sample eluted from said succeeding chromatography apparatus, an ion sort having a specified mass versus charge ratio m/z is selected from various sorts of ions and dissociated at a time point of holding time which is obtained from data of chromatogram of said preceding chromatography apparatus and at which the ionic strength is near a peak and further tandem mass spectroscopy is conducted by repeating selection, dissociation and measurement of an ion sort to be measured in multiple stages.

8. A mass spectrometric method according to claim 1, wherein a holding time at which the ionic strength of an ion having a mass number versus charge value m/z is near a peak is calculated within a real time of measurement on the basis of data indicative of detected strengths of ions of sample constituents passing through said preceding chromatography apparatus and determined in respect of individual mass number versus charge values m/z of the ions and for a sample eluted from the succeeding chromatography apparatus, an ion having a certain mass number versus charge value m/z is selected and dissociated at a time point of holding time which is obtained from the chromatograph data of the preceding chromatography apparatus and at which the strength of the ion having the mass number versus charge value m/z is near a peak and further tandem mass spectrometry is carried out by repeating selection, dissociation and measurement of an ion sort to be measured in multiple stages.

9. A mass spectrometric method according to claim 1, wherein the timing of holding time at which the ion strength, obtained from the chromatogram data of said preceding chromatography apparatus, is near the peak is in a range of a predetermined time following start of detection of the ion and being more than a time for half-width (ΔT) at the peak of ion strength and less than several times or several of tens of times the half-width time.

10. A mass spectroscopy method according to claim 1, wherein a sample subject to mass spectrometry is a biopolymer related substance.

11. A mass spectrometry method according to claim 1, wherein a sample subject to mass spectrometry is a low molecular weight substance.

12. A mass spectrometric system comprising:
a plurality of chromatography apparatus having elusion start times set to be mutually different;
a tandem mass spectrometer for performing mass spectrometry of samples eluted from said chromatography apparatus; and
a controller for commanding that chromatogram data obtained from preceding one of said plurality of chromatography apparatus be subjected to an analysis process within a real time during measurement and that a mass spectrometry condition and/or mass spectrometry contents when a sample eluted from another chromatography apparatus be changed on real time on the basis of results of the analysis process.

13. A mass spectrometric system according to claim 12 further comprising an internal database connected to said controller to store the results of spectrometry by said chromatography apparatus and tandem mass spectrometer and the changed condition and/or contents.

14. A mass spectrometric system according to claim 12 further comprising an input unit for enabling a user to input a start time difference of said succeeding chromatography apparatus from said preceding chromatography apparatus or a display unit for displaying start time.

15. A mass spectrometric system according to claim 12 further comprising a user interface for enabling a user to designate a spectrometry condition and/or spectrometry contents when a decision is made as to whether the function of changing or adjusting a spectrometry condition and/or spectrometry contents is to be executed at the time that a sample having passed through said succeeding chromatography apparatus is subjected to mass spectrometry or said function is executed.

16. A mass spectrometric system according to claim 12 in which a single mass spectrometer is arranged for said plurality of chromatography apparatus,
wherein means for switching over individual samples eluted from said plurality of chromatography apparatus and said samples from the individual chromatography apparatus are alternately subjected to mass spectrometry.

17. A mass spectrometric system according to claim 12 in which a plurality of chromatography apparatus and a plurality of mass spectrometers are provided, wherein at least two of said plurality of chromatography apparatus have mutually shifted elusion start times and are arranged such that samples from the individual chromatography apparatus are flown into individual mass spectrometers so as to be subjected to mass spectrometry and a spectrometry condition and/or spectrometry contents of each mass spectrometer is changed and adjusted by results of measurement by another chromatography apparatus and another mass spectrometer.

18. A mass spectrometric system according to claim 12, wherein said mass spectrometer is an ion trap type or linear trap type mass spectrometer.

19. A mass spectrometric system according to claim 12, wherein said mass spectrometer is an ion trap-time on flight type mass spectrometer or linear trap-time on flight time type mass spectrometer.

20. A mass spectrometric system according to claim 12, wherein said mass spectrometer is a quadruple mass spectrometer having, as a mechanism for selecting and dissociating an ion having a specified mass versus charge ratio, a mechanism of CID and/or ECD.

* * * * *